(12) United States Patent
Suzuki et al.

(10) Patent No.: US 10,955,571 B2
(45) Date of Patent: Mar. 23, 2021

(54) RADIOGRAPHING APPARATUS AND RADIOGRAPHING SYSTEM

(71) Applicant: CANON KABUSHIKI KAISHA, Tokyo (JP)

(72) Inventors: Masataka Suzuki, Yokohama (JP); Atsushi Takeuchi, Kawasaki (JP); Hiroto Kondo, Machida (JP); Shichihei Sakuragi, Kawasaki (JP); Akiya Nakayama, Kawasaki (JP); Katsushi Kato, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 16/355,431

(22) Filed: Mar. 15, 2019

(65) Prior Publication Data
US 2019/0293812 A1    Sep. 26, 2019

(30) Foreign Application Priority Data

Mar. 20, 2018  (JP) .............................. JP2018-052276
Mar. 20, 2018  (JP) .............................. JP2018-052297

(51) Int. Cl.
| | |
|---|---|
| *G01T 7/00* | (2006.01) |
| *G01T 1/00* | (2006.01) |
| *H02J 50/00* | (2016.01) |
| *H05K 5/02* | (2006.01) |
| *H05K 5/04* | (2006.01) |
| *H02J 7/02* | (2016.01) |

(52) U.S. Cl.
CPC ................ *G01T 7/00* (2013.01); *H02J 50/00* (2016.02); *H05K 5/02* (2013.01); *H05K 5/04* (2013.01); *G01T 1/00* (2013.01); *H02J 7/025* (2013.01)

(58) Field of Classification Search
CPC .... G01T 1/00; G01T 7/00; H02J 50/00; H02J 7/025; H05K 5/02; H05K 5/04
See application file for complete search history.

(56) References Cited

U.S. PATENT DOCUMENTS

| | | | | |
|---|---|---|---|---|
| 2010/0034351 | A1* | 2/2010 | Yanagita | .............. A61B 6/4216 378/62 |
| 2010/0148085 | A1* | 6/2010 | Yoshida | .................... G01T 1/00 250/395 |

(Continued)

FOREIGN PATENT DOCUMENTS

| | | |
|---|---|---|
| JP | 2014-068471 A | 4/2014 |
| JP | 2015-166691 A | 9/2015 |

*Primary Examiner* — David P Porta
*Assistant Examiner* — Fani Booalis
(74) *Attorney, Agent, or Firm* — Canon U.S.A., Inc. IP Division

(57) ABSTRACT

A radiographing apparatus includes a radiation detection panel that detects radiation, a casing that encloses the radiation detection panel, and a wireless power reception portion. The casing includes an entrance portion via which radiation enters, a bottom portion arranged on the opposite side of the entrance portion, and a plurality of side portions. The casing also includes a connection portion that continuously connects the bottom portion and the side portions at a position located inside a first extension plane, which is an extension of the surface of the bottom portion, and a second extension plane, which is an extension of the surface of the side portions. The wireless power reception portion is arranged at the connection portion.

24 Claims, 17 Drawing Sheets

(56) References Cited

U.S. PATENT DOCUMENTS

| | | | |
|---|---|---|---|
| 2011/0042574 A1* | 2/2011 | Nishino | A61B 6/4266 250/370.08 |
| 2014/0226795 A1* | 8/2014 | Kitano | A61B 6/4283 378/189 |
| 2014/0231664 A1* | 8/2014 | Howe | G01T 7/00 250/395 |

* cited by examiner

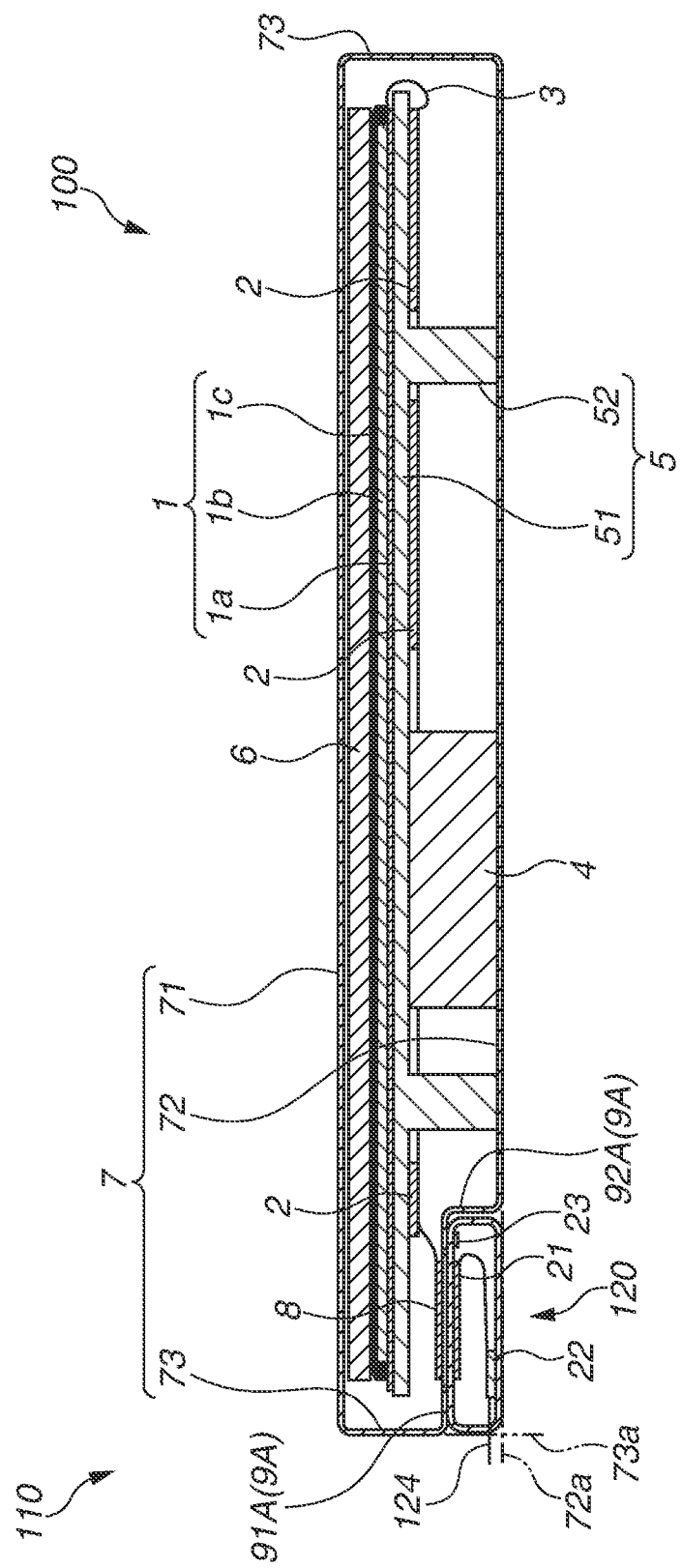

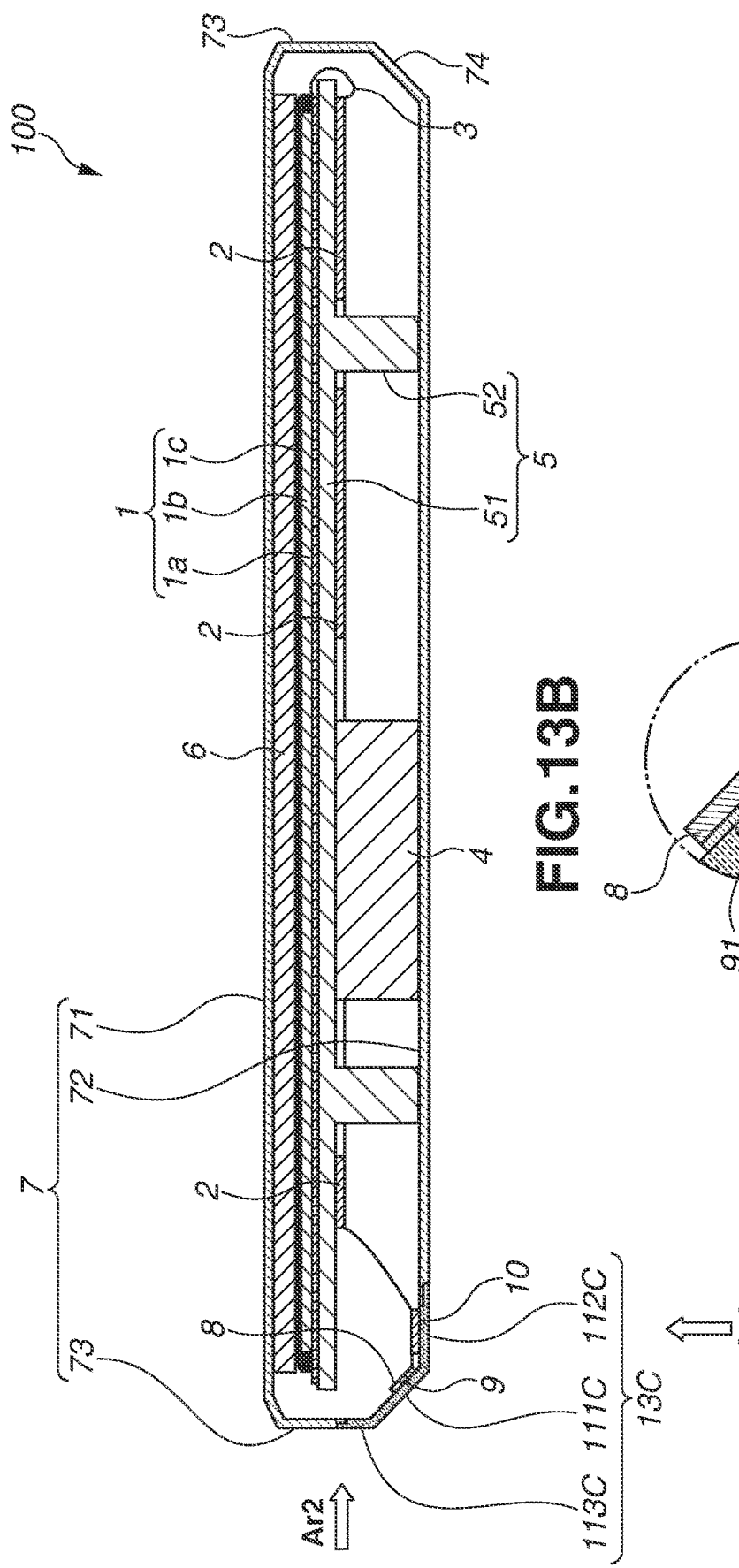

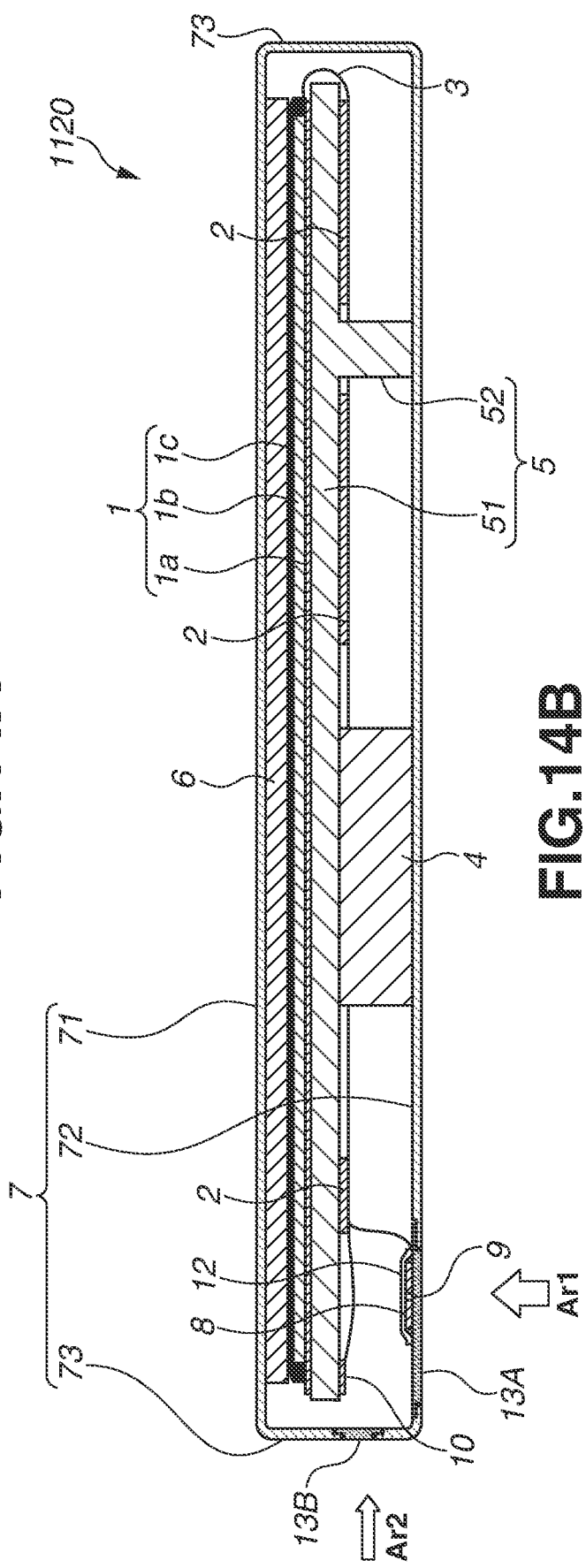

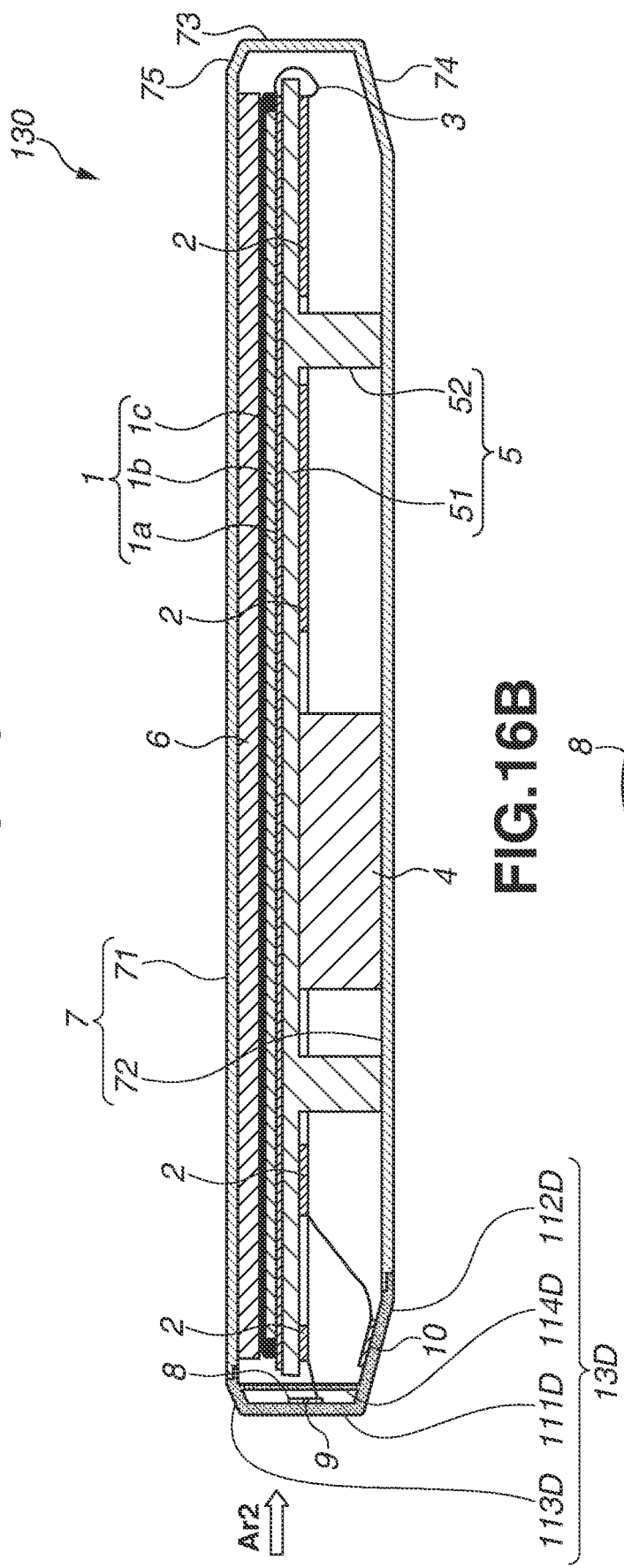
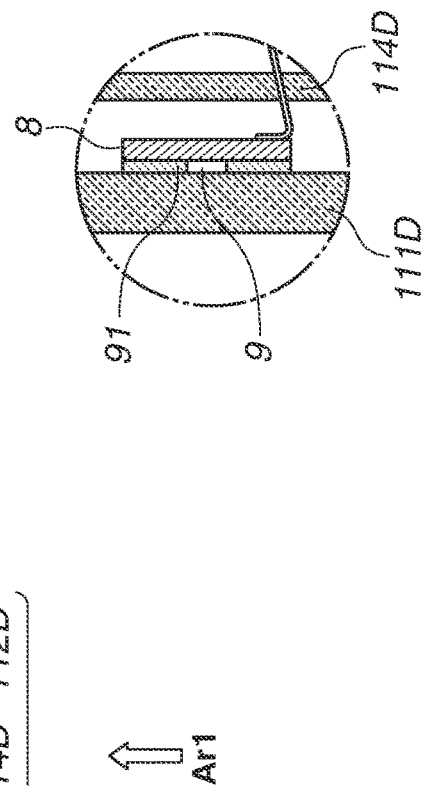

RADIOGRAPHING APPARATUS AND RADIOGRAPHING SYSTEM

BACKGROUND

Field

The present disclosure relates to a radiographing apparatus and a radiographing system.

Description of the Related Art

A radiographing apparatus configured to acquire a radiographic image by detecting an intensity distribution of radiation transmitted through a target is widely used in industrial non-destructive inspection and medical diagnosis.

Japanese Patent Application Laid-Open No. 2015-166691 discusses a radiographing apparatus that wirelessly receives power necessary for a radiation sensor panel and an electric substrate, and also to prevent water from entering the radiographing apparatus and to prevent electrical leakages. The radiographing apparatus includes a holding portion configured to hold a wireless power transmission portion to perform stable contactless power reception with ease.

Japanese Patent Application Laid-Open No. 2014-068471 discusses a wireless power reception/supply apparatus configured to perform wireless charging and wireless data transfer.

In the radiographing apparatus discussed in Japanese Patent Application Laid-Open No. 2015-166691, a wireless power reception portion is located in a depressed portion formed in the bottom surface of the imaging apparatus, which can result in in difficulty accessing the wireless power reception portion. For example, in a case in which the imaging apparatus is set on a holder of an imaging table or the bottom surface of the imaging apparatus is placed to be in contact with a flat surface, such as the imaging table, the depressed portion is hidden behind the holder or the flat surface, which makes the wireless power reception portion less accessible.

There is a radiographing apparatus covered with a casing made of an alloy of a metal, such as aluminum or magnesium, or carbon fiber reinforced plastic (CFRP) in order to increase strength against impact force and external force. Such a conductive casing blocks electromagnetic waves for use in wireless data transfer and charging, and this leads to a decrease the efficiency in transfer. Thus, the conductive casing needs to include a window portion made of a non-conductive material. In a case in which an indicator using a light source such as a light emitting diode (LED) is provided, since a metal alloy and CFRP do not transmit light, the casing needs to include a window portion made of a light-transmissive material. Forming a large number of such window portions results in the casing having a plurality of holes and surfaces with non-uniform strength, which can lead to a decrease in strength of the imaging apparatus.

SUMMARY

The present disclosure is directed to a technique for preventing a decrease in strength of a radiographing apparatus and increasing accessibility to a wireless power reception portion.

According to an aspect of the present disclosure, a radiographing apparatus, includes a radiation detection panel configured to detect radiation, a casing configured to enclose the radiation detection panel, and a wireless power reception portion, wherein the casing includes an entrance portion through which the radiation enters, a bottom portion arranged on an opposite side of the entrance portion, a plurality of side portions, a connection portion configured to continuously connects the bottom portion and the side portions at a position located inside a first extension plane, which is an extension of a surface of the bottom portion, and a second extension plane, which is an extension of a surface of the side portions, wherein the wireless power reception portion is arranged at the connection portion.

Further features will become apparent from the following description of exemplary embodiments with reference to the attached drawings.

BRIEF DESCRIPTION OF THE DRAWINGS

FIG. 3 is a cross-sectional view illustrating an example of a radiographing system according to the first exemplary embodiment.

FIGS. 13A and 13B are cross-sectional views illustrating an example of the radiographing apparatus according to the modified example of the fourth exemplary embodiment.

FIGS. 14A and 14B are cross-sectional views illustrating an example of a radiographing apparatus according to a fifth exemplary embodiment.

FIGS. 16A and 16B are cross-sectional views illustrating an example of the radiographing apparatus according to the sixth exemplary embodiment.

DESCRIPTION OF THE EMBODIMENTS

Various exemplary embodiments will be described in detail below with reference to the drawings. The details of dimensions and structures specified in the exemplary embodiments are not limited to those specified in the present specification or drawings. The term "radiation" as used herein refers to not only an X-ray, but also an alpha ray, beta ray, gamma ray, particle ray, and cosmic ray.

A radiographing apparatus (hereinafter, "imaging apparatus") 100 according to a first exemplary embodiment will be described with reference to FIGS. 1A to 4B.

Figure 1A:
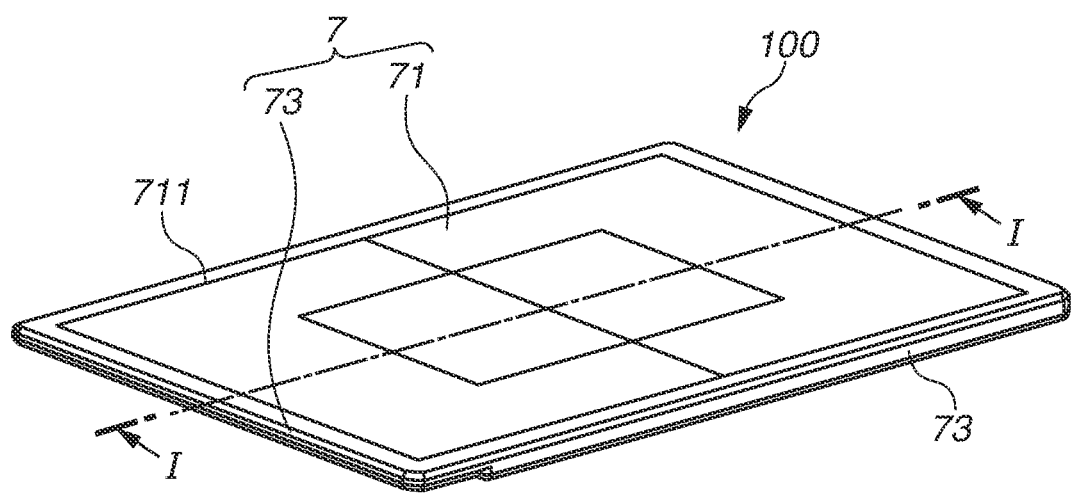
FIGS. 1A and 1B are external views illustrating an example of a radiographing apparatus according to a first exemplary embodiment.
Figure 1B:
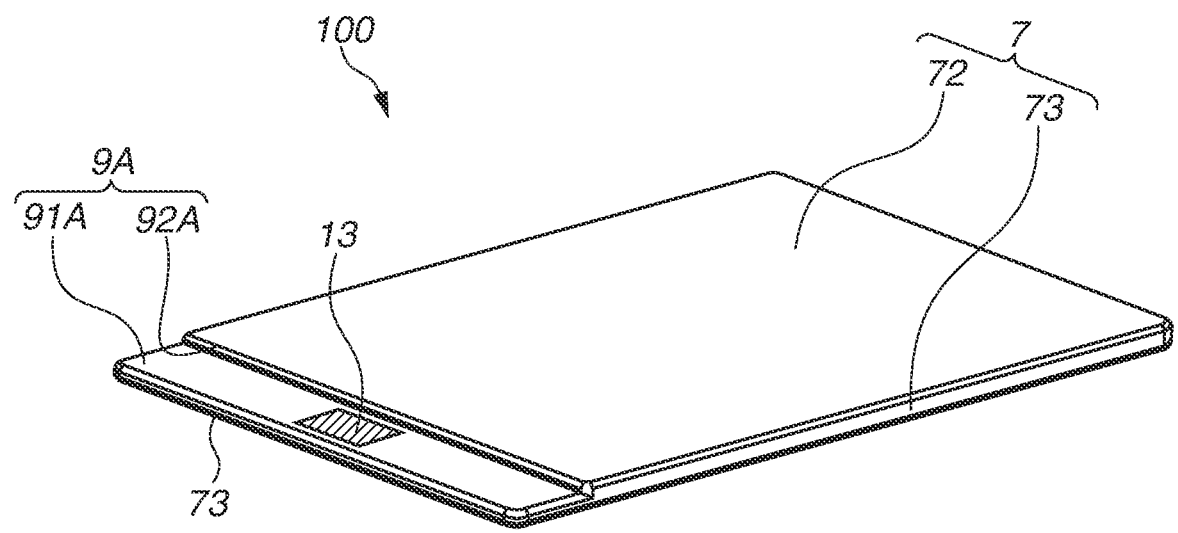
Figure 2:
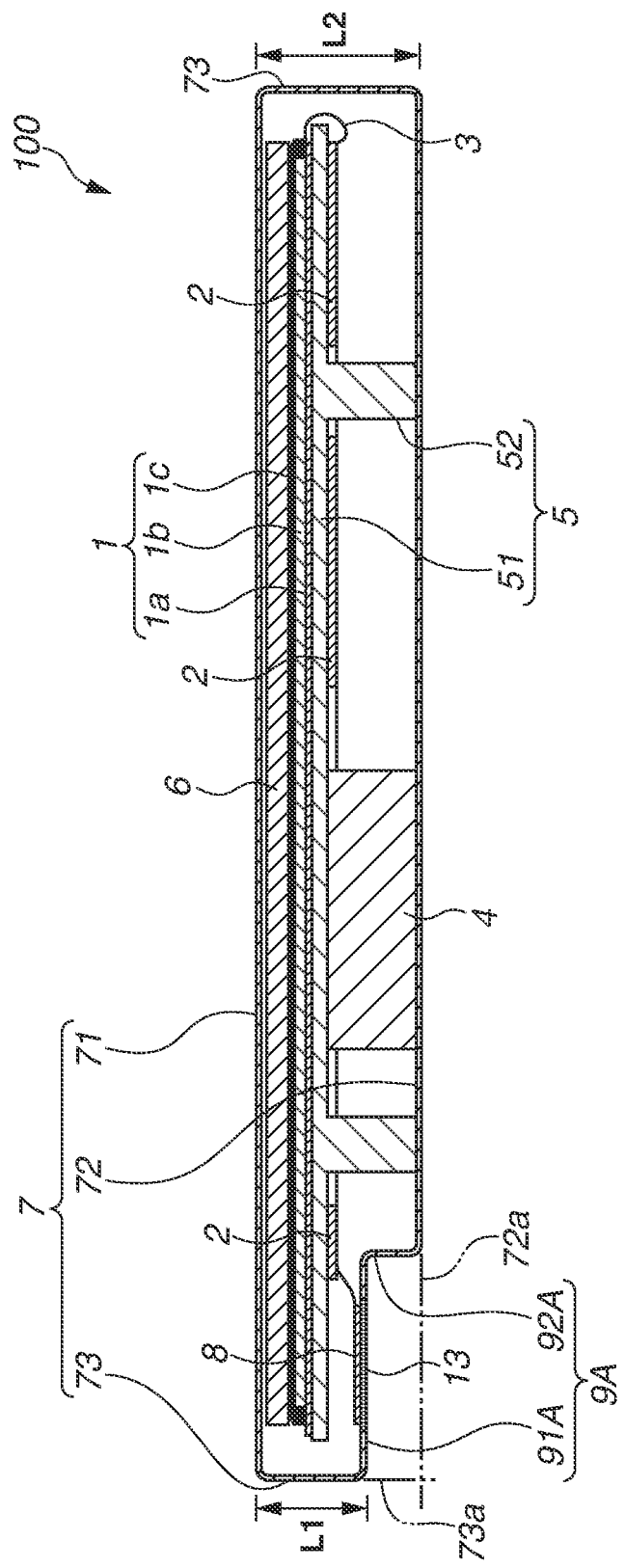
FIG. 2 is a cross-sectional view illustrating an example of the radiographing apparatus according to the first exemplary embodiment.

FIG. 1A is an external view illustrating the imaging apparatus 100 viewed from a radiation incident direction. FIG. 1B is an external view illustrating the imaging apparatus 100 viewed from the opposite side to that in FIG. 1A. FIG. 2 is a cross-sectional view illustrating a cross-section that is cut along a line I-I in FIG. 1A and viewed from an arrow direction.

The imaging apparatus 100 acquires a radiographic image corresponding to a radiation emitted from a radiation generation apparatus (not illustrated) and transmitted through a subject. The imaging apparatus 100 transfers the acquired radiographic image data to an external apparatus and displays an image corresponding to the data on an external display apparatus.

The imaging apparatus 100 includes a radiation detection panel (hereinafter, referred to as "detection panel") 1, a control substrate 2, a secondary battery 4, a support base 5, a buffer material 6, a casing 7, and a wireless power reception portion 8.

The detection panel 1 converts incident radiation into an image signal. The detection panel 1 has a detection surface on a radiation incident side. The detection panel 1 includes a sensor substrate 1a, a phosphor layer 1b, and a phosphor protection film 1c. The sensor substrate 1a includes a plurality of photoelectric conversion elements arranged two-dimensionally on a glass substrate. The phosphor layer 1b is arranged on the sensor substrate 1a, and the phosphor protection film 1c is arranged on the phosphor layer 1b. Metal-insulator-semiconductor (MIS) or positive-intrinsic-negative (PIN) conversion elements capable of detecting visible light are used as the plurality of photoelectric conversion elements arranged on the sensor substrate 1a. The phosphor protection film 1c protects the phosphor layer 1b. A material having a comparatively high moisture-resistance is used as a material of the phosphor protection film 1c.

The detection panel 1 includes an effective imaging region that converts incident radiation into a radiographic image. An entire or partial region of a flat surface of the detection panel 1, on which the plurality of photoelectric conversion elements is arranged when viewed from the radiation incident direction, is set as the effective imaging region.

In the detection panel 1 having the above-described structure, incident radiation causes the phosphor layer 1b to emit light, and the emitted light is converted into an electric signal by the photoelectric conversion elements arranged on the sensor substrate 1a. Alternatively, the detection panel 1 can use a direct-conversion type conversion elements configured to convert radiation directly into an electric signal, in place of the phosphor layer 1b and the photoelectric conversion elements.

The detection panel 1 is electrically connected to the control substrate 2 via a flexible circuit substrate 3.

The control substrate 2 reads the electric signal converted by the detection panel 1 and processes the read electric signal. The control substrate 2 converts the electric signal into a digital signal to thereby acquire radiographic image data.

The secondary battery 4 supplies power for use in operations of the detection panel 1 and the control substrate 2. The secondary battery 4 has a function as a battery. For example, a lithium ion battery, electric double-layer capacitor, or all-solid-state battery is used as the secondary battery 4.

The support base 5 supports the components of the imaging apparatus 100 in the casing 7. The support base 5 includes a substrate support portion 51 and a leg portion 52. The substrate support portion 51 is formed, for example, in a shape of a flat plate, and a surface of the substrate support portion 51, which is on the radiation incident surface side, supports the detection panel 1. A surface of the substrate support portion 51 that is on the opposite side to the surface supporting the detection panel 1 supports the control substrate 2 and the secondary battery 4. The leg portion 52 extends from the surface that is on the opposite side to the surface supporting the detection panel 1, and is joined to the casing 7.

The buffer material 6 protects the detection panel 1 from external force. The buffer material 6 is arranged between the detection surface of the detection panel 1 and the casing 7.

The casing 7 encloses the components of the imaging apparatus 100.

The casing 7 is substantially cuboid and has a substantially rectangular shape having longer and shorter sides when viewed from the radiation incident direction. The casing 7 has an entrance portion 71, a bottom portion 72, and a plurality of side portions 73 (e.g., four side portions). The entrance portion 71 is where radiations enter. The bottom portion 72 is arranged on the opposite side to the entrance portion 71 via the detection panel 1. The plurality of side portions 73 connects the entrance portion 71 and the bottom portion 72. The casing 7 can be formed by, for example, forming the bottom portion 72 and the side portions 73 as an integrated portion and joining the integrated portion to the entrance portion 71 formed as a separate portion.

Radiation enters the entrance portion 71. The entrance portion 71 is substantially plate-shaped having an externally-exposed surface (outer surface), which is substantially flat. In order to enable radiation to enter, the entrance portion 71 desirably has a relatively high radiation transmittance. The entrance portion 71 is desirably light in weight and has a predetermined strength against impact. For example, a resin material or carbon fiber reinforced plastic (CFRP) is used as a material of the entrance portion 71.

On the surface of the entrance portion 71, an index 711 is written to specify a central portion and range of the effective imaging region. The index 711 is formed by painting or printing processing. A user can recognize the central portion of the effective imaging region and the effective imaging region with ease by seeing the index 711. The index 711 can be any index from which a user can recognize the central portion and range of the effective imaging region, and the index 711 can be, for example, a step depressed in the direction of the detection panel 1.

The bottom portion 72 covers the components of the imaging apparatus 100 from the opposite side to the entrance portion 71. The bottom portion 72 is substantially plate-shaped with an externally exposed surface (outer surface) that is substantially flat. The bottom portion 72 is substantially parallel to the entrance portion 71. The bottom portion 72 includes a plate-shaped portion located farthest from the entrance portion 71 but does not include a first connection portion 91A described below.

The side portions 73 cover the components of the imaging apparatus 100 from the sides. The side portions 73 are substantially plate-shaped with an externally exposed surface (outer surface) that is substantially flat. The side portions 73 are substantially orthogonal to the entrance portion 71 and the bottom portion 72. The side portions 73 include a portion that is continuous to the entrance portion 71 but do not include a second connection portion 92A described below.

The bottom portion 72 and the side portions 73 desirably have a predetermined drop impact strength, are light in weight to reduce a burden during conveyance, and are highly operable. Examples of a material used as a material of the bottom portion 72 and the side portions 73 include an alloy of metals, such as magnesium or aluminum, CFRP, and fiber-reinforced resin. A material having a relatively high permeability, such as stainless steel (SUS430), can be used as a material of the bottom portion 72 and the side portions 73 in order to effectively reduce noise received from the outside of the casing 7.

The wireless power reception portion 8 receives wirelessly-transmitted power to thereby charge the secondary battery 4. Thus, the secondary battery 4 is charged as appropriate so that a sufficient amount of power is stored at the time of imaging and thus a user can smoothly perform radiographing. As illustrated in FIG. 1B, the casing 7 includes a window portion 13 near the wireless power reception portion 8.

The window portion 13 increases efficiency in power reception by the wireless power reception portion 8. A material that can be used as a material of the window portion 13 is a non-conductive material and, for example, a resin or fiber-reinforced resin can be used. In a case in which the casing 7 is not conductive, the window portion 13 may not be needed.

Next, a structure of the casing 7 in which the wireless power reception portion 8 is arranged will be described.

The casing 7 according to the present exemplary embodiment includes a portion at which the bottom portion 72 and the side portions 73 are not directly continuous to each other. In other words, the casing 7 includes a connection portion 9A that continuously connects the bottom portion 72 and the side portions 73. As used herein, the phrase "continuously connects" indicates that neither the bottom portion 72 nor the side portions 73 exist between the bottom portion 72 and the side portions 73. If the bottom portion 72 exists again between the bottom portion 72 and the side portions 73, a depressed portion is formed between the two bottom portions 72. If the side portion 73 exits again between the bottom portion 72 and the side portion 73, a depressed portion is formed between the two side portions 73.

Thus, as illustrated in FIG. 2, at the portion where the connection portion 9A is formed, the bottom portion 72 is not continuous to the side portions 73 without the connection portion 9A. Similarly, the side portion 73 is not continuous to the bottom portion 72 without the connection portion 9A. In such a structure, a length L1 (length in the thickness direction of the imaging apparatus 100) of the side portion 73 to which the connection portion 9A is formed is shorter than a length L2 of the side portion 73 that is arranged on the opposite side.

As illustrated in FIG. 2, the connection portion 9A according to the present exemplary embodiment is located inside a first extension plane 72a extending from the surface of the bottom portion 72, i.e., on the casing 7 side, and the connection portion 9A is located inside a second extension plane 73a extending from the surface of the side portions 73, i.e., on the casing 7 side.

Specifically, the connection portion 9A includes the first connection portion 91A and the second connection portion 92A.

As illustrated in FIG. 2, the first connection portion 91A is continuous to the side portion 73 and the second connection portion 92A. The first connection portion 91A is substantially plate-shaped with an externally exposed surface (outer surface) that is substantially flat. The first connection portion 91A is substantially parallel to the entrance portion 71 and the bottom portion 72.

The structure of the first connection portion 91A is not limited to the structure in which the first connection portion 91A is substantially parallel to the entrance portion 71 and the bottom portion 72, and the first connection portion 91A can be inclined as long as the first connection portion 91A is located inside the first extension plane 72a and the second extension plane 73a.

The second connection portion 92A is continuous to the bottom portion 72 and the first connection portion 91A. The second connection portion 92A is substantially plate-shaped with an externally exposed surface (outer surface) that is substantially flat. The second connection portion 92A is substantially parallel to the side portions 73.

The structure of the second connection portion 92A is not limited to the structure in which the second connection portion 92A is substantially parallel to the side portions 73, and the second connection portion 92A can be inclined as long as the second connection portion 92A is located inside the first extension plane 72a and the second extension plane 73a.

According to the present exemplary embodiment, the wireless power reception portion 8 is arranged on the connection portion 9A. More specifically, the wireless power reception portion 8 is arranged on a surface (inner surface) of the first connection portion 91A that is not externally exposed. As described above, the wireless power reception portion 8 is arranged on the connection portion 9A so that accessibility to the wireless power reception portion 8 increases. Thus, even in the case in which the imaging apparatus 100 is set on the holder of the imaging table or the bottom portion 72 is placed to be in contact with the table for imaging, a user can access the wireless power reception portion 8 through a space formed by the connection portion 9A from the side portion 73 that is located on the side where the connection portion 9A is located.

As illustrated in FIG. 1B, the connection portion 9A according to the present exemplary embodiment is continuous not only to the side portion 73 of the shorter side but also to the side portions 73 of the longer sides adjacent to the side portion 73 of the shorter side. In other words, the connection portion 9A is continuous to the three side portions 73. As described above, the wireless power reception portion 8 is arranged on the connection portion 9A formed to be continuous to the three side portions 73 so that the wireless power reception portion 8 is accessible from any one of the three side portions 73. Thus, accessibility to the wireless power reception portion 8 from a plurality of directions is increased. The structure of the connection portion 9A is not limited to the structure in which the connection portion 9A is continuous to the three side portions 73, and the connection portion 9A can be formed to be continuous to one or two side portions 73.

According to the present exemplary embodiment, the wireless power reception portion 8 is arranged on the first connection portion 91A, which is substantially parallel to the bottom portion 72. The imaging apparatus 100 has a flat shape that is wider in the direction parallel to the bottom portion 72 than in the thickness direction. As a result, the first connection portion 91A, which is substantially parallel to the bottom portion 72, can have a larger space for placing the wireless power reception portion 8, compared to the second connection portion 92A arranged along the thickness direction. This enables increasing the mounting size of the wireless power reception portion 8 to thereby increase the amount of power to be received by the wireless power reception portion 8.

According to the present exemplary embodiment, the wireless power reception portion 8 is arranged to not overlap the control substrate 2 and the flexible circuit substrate 3 when viewed from the radiation incident direction (refer to FIG. 2). This prevents a magnetic field generated at the time of wireless charging from affecting other electric signals and control signals. The control substrate 2 and the flexible circuit substrate 3 are examples of a circuit substrate.

There is a case in which an external grid is attached to the imaging apparatus 100. At this time, a holding frame that holds the grid can partly cover the side portions 73 of the casing 7. In this case, the wireless power reception portion 8 can become less accessible. Thus, a maximum depth (distance from the outer surface of the bottom portion 72 to the outer surface of the first connection portion 91A) of the first connection portion 91A is desirably about a half (half or less) of the thickness of the imaging apparatus 100. More specifically, the maximum depth of the first connection portion 91A is desirably 8 mm or less at a maximum from the bottom portion 72. As described above, the maximum depth of the first connection portion 91A is not set deep to thereby increase accessibility to the wireless power reception portion 8 even in the case in which the grid is attached.

Next, a radiographing system (hereinafter, "imaging system") 110 will be described.

FIG. 3 is a cross-sectional view illustrating an example of a configuration of the imaging system 110.

The imaging system 110 includes the imaging apparatus 100 and a wireless power transmission unit 120. The structure of the imaging apparatus 100 is similar to the above-described structure, and the same reference numerals are used and description thereof is omitted.

The wireless power transmission unit 120 wirelessly transmits power to the wireless power reception portion 8. The wireless power transmission unit 120 includes a wireless power transmission portion 21, a control substrate 22, a magnet 23, and a wired cable 124.

Power is externally supplied to the wireless power transmission portion 21, and the wireless power transmission portion 21 transmits the power to the wireless power reception portion 8. The control substrate 22 controls the wireless power transmission portion 21. The magnet 23 functions as a positioning member. The magnet 23 is arranged in the casing 7 of the wireless power transmission unit 120 and enables the wireless power transmission unit 120 to be attached to and removed from the imaging apparatus 100. More specifically, the magnet 23 is attached to position the wireless power transmission unit 120 with respect to the imaging apparatus 100 such that the wireless power transmission portion 21 and the wireless power reception portion 8 face each other. At this time, the wireless power transmission portion 21 and the wireless power reception portion 8 are in a state in which only the outer surfaces of the wireless power transmission portion 21 and the wireless power reception portion 8 are in contact with each other, so that the freedom in aligning the wireless power transmission unit 120 to the wireless power reception portion 8 increases.

Meanwhile, in the state in which the wireless power transmission unit 120 is positioned with respect to the imaging apparatus 100 as illustrated in FIG. 3, the size of the wireless power transmission unit 120 (casing 7) does not extend beyond the first extension plane 72a and the second extension plane 73a. The size of the wireless power transmission unit 120 (casing 7) is desirably within the first extension plane 72a and the second extension plane 73a. The wireless power transmission unit 120 is structured as described above, so that the wireless power transmission unit 120 can be set on the holder of the imaging table even at the time of wireless charging.

While power is supplied to the wireless power transmission unit 120 by the wired cable 124 and the wired cable 124 is located outside the first extension plane 72a and the second extension plane 73a in FIG. 3, the configuration is not limited to that illustrated in FIG. 3. For example, the wireless power transmission unit 120 can include an internal secondary battery to supply power. In this way, the wireless power transmission unit 120 can be arranged to not extend beyond the first extension plane 72a and the second extension plane 73a thoroughly.

Next, an imaging apparatus 130 according to a modified example of the first exemplary embodiment will be described with reference to FIGS. 4A and 4B. While the imaging apparatus 100 illustrated in FIGS. 1A, 1B, and 2 includes only one connection portion 9A, the imaging apparatus 130 in FIGS. 4A and 4B includes a plurality of connection portions 9B and 9C. Components similar to those in FIGS. 1A, 1B, and 2 are given the same reference numerals.

Figure 4A:
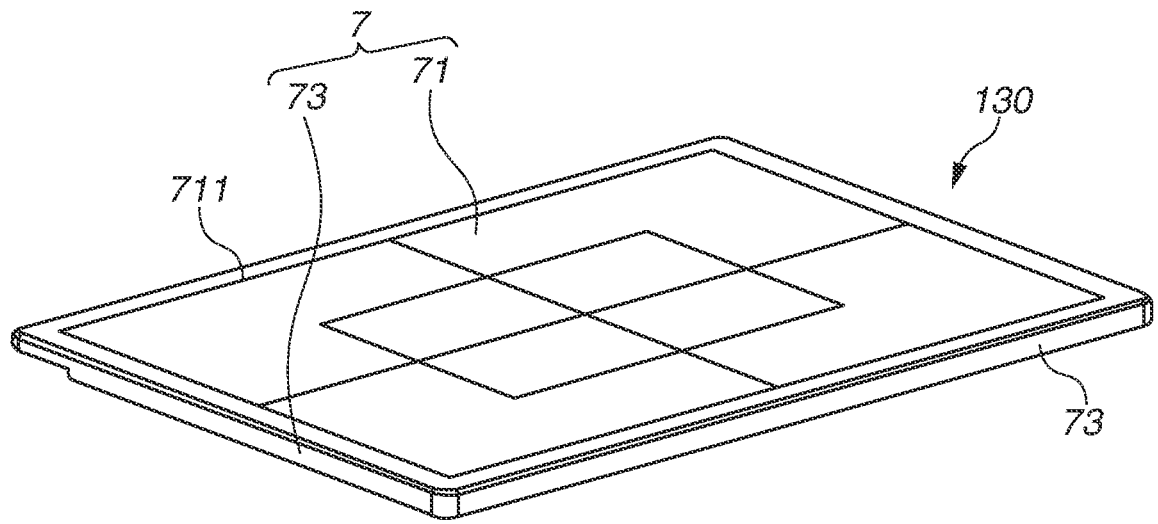
FIGS. 4A and 4B are external views illustrating an example of a radiographing apparatus according to a modified example of the first exemplary embodiment.

FIG. 4A is an external view illustrating the imaging apparatus 130 viewed from the radiation incident direction. FIG. 4B is an external view illustrating the imaging apparatus 130 viewed from the opposite side of imaging apparatus 130 viewed in FIG. 4A.

Figure 4B:
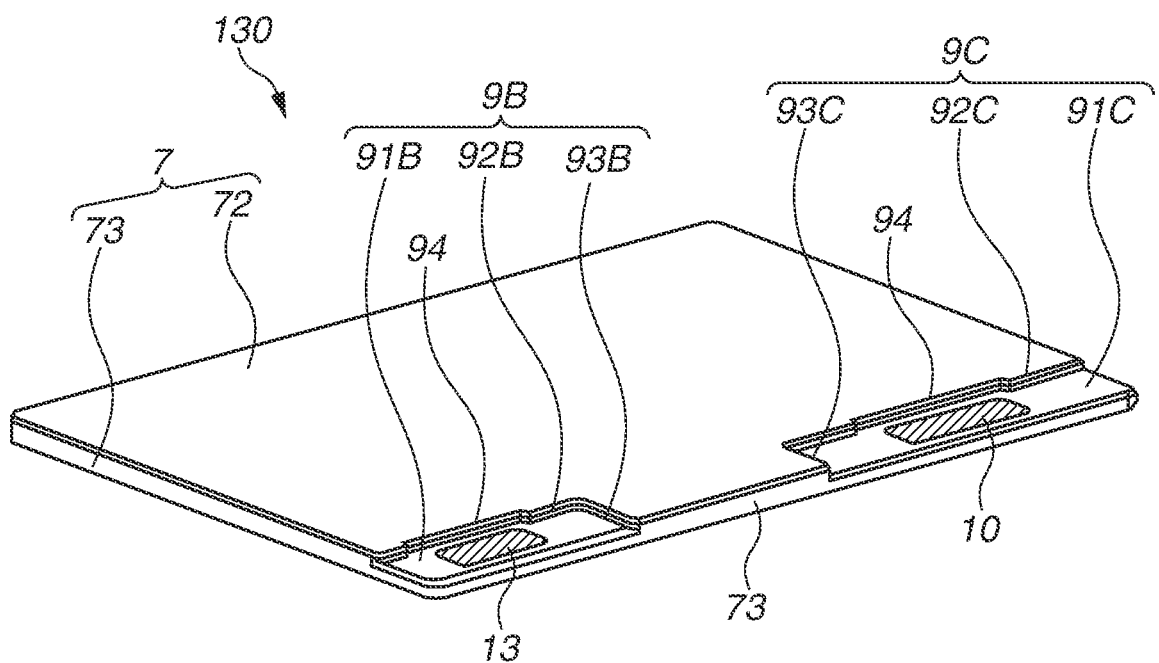

As illustrated in FIG. 4B, the casing 7 of the imaging apparatus 130 includes two connection portions 9B and 9C. The two connection portions 9B and 9C are separately positioned.

First, the connection portion 9B continuously connects the bottom portion 72, the side portion 73 of the shorter side, and the side portion 73 of the longer side. The connection portion 9B includes a first connection portion 91B, a second connection portion 92B, and a third connection portion 93B. The first connection portion 91B is substantially parallel to the entrance portion 71 and the bottom portion 72. The second connection portion 92B is substantially parallel to the side portion 73 of the longer side, whereas the third connection portion 93B is substantially parallel to the side portion 73 of the shorter side. The second connection portion 92B includes a depressed portion 94 formed so as to avoid the window portion 13.

Next, the connection portion 9C continuously connects the bottom portion 72, the side portion 73 of the shorter side, and the side portion 73 of the longer side. The connection portion 9C includes a first connection portion 91C, a second connection portion 92C, and a third connection portion 93C. The first connection portion 91C is substantially parallel to the entrance portion 71 and the bottom portion 72. The second connection portion 92C is substantially parallel to the side portion 73 of the longer side, whereas the third connection portion 93C is substantially parallel to the side portion 73 of the shorter side. The second connection portion 92C includes the depressed portion 94 formed so as to avoid the window portion 13, as in the second connection portion 92B.

The first connection portions 91B and 91C each include the window portion 13. The wireless power reception portion 8 is arranged on the inside of each window portion 13. Thus, the wireless power reception portion 8 is arranged at each of the connection portions 9B and 9C so that accessibility to the wireless power reception portion 8 increases.

The number and positions of the connection portions 9B and 9C are not limited to those described above. For example, there can be three or more connection portions, and at least two connection portions can be arranged at opposite corners of the rectangular shape of the casing 7. The maximum depths (distances from the outer surface of the bottom portion 72 to the outer surfaces of the first connection portions 91B and 91C) of the plurality of connection portions do not have to be the same.

A depressed or protruding portion for positioning with respect to the wireless power transmission unit 120 can be provided to some of the first connection portions 91B and 91C, the second connection portions 92B and 92C, or the third connection portions 93B and 93C. The position and size of the depressed or protruding portion for positioning are desirably set so to not decrease accessibility and freedom in the insertion/removal direction.

The connection portions 9B and 9C also function as a handle portion for holding the imaging apparatus 100 when the imaging apparatus 130 is placed on a flat place, which increases usability. Thus, the imaging apparatus 130 can include a single or a plurality of connection portions without the wireless power reception portion 8 arranged.

An imaging apparatus 140 according to a second exemplary embodiment will be described with reference to FIGS. 5A to 5C.

Figure 5A:
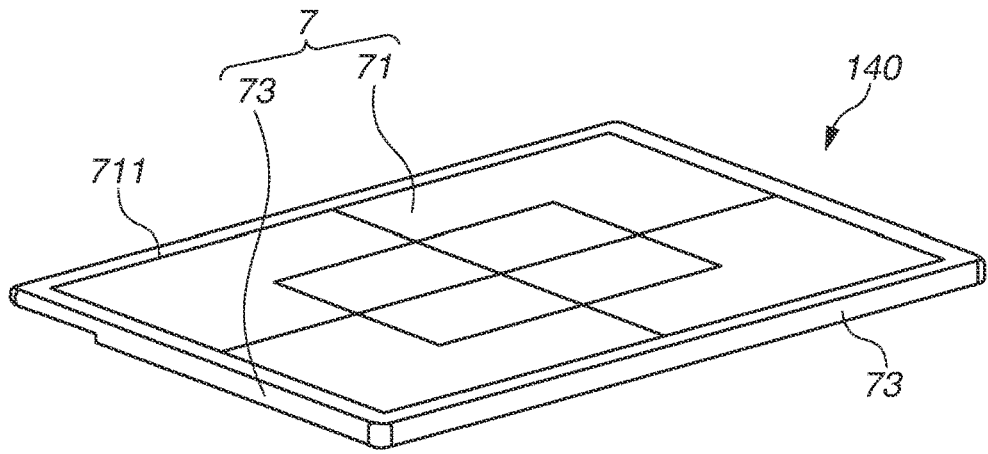
FIGS. 5A, 5B, and 5C are external views illustrating an example of a radiographing apparatus according to a second exemplary embodiment.
Figure 5B:
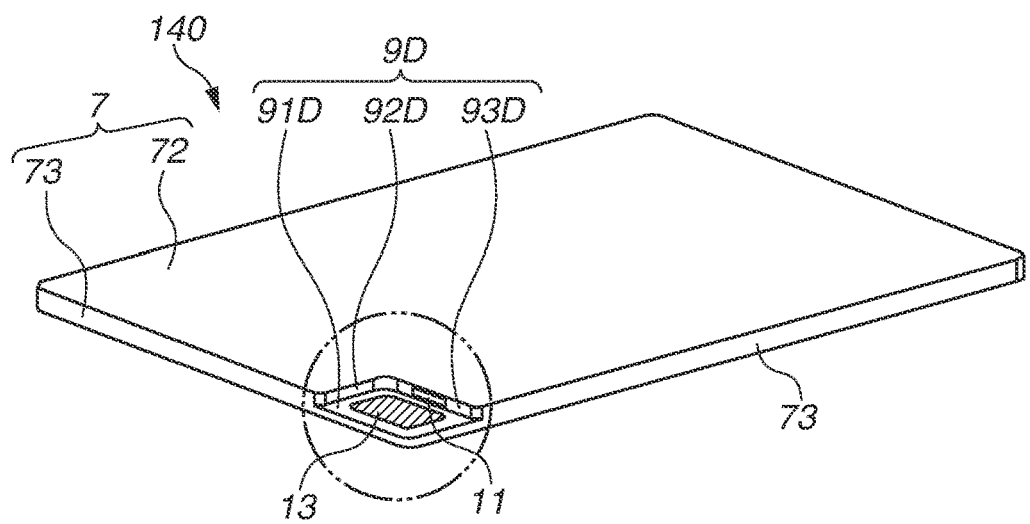

FIG. 5A is an external view illustrating the imaging apparatus 140 viewed from the radiation incident direction. FIG. 5B is an external view illustrating the imaging apparatus 140 viewed from the opposite side of the imaging apparatus 140 viewed in to FIG. 5A. FIG. 5C is an enlarged view of a portion in a circle specified by a two-dot chain line in FIG. 5B. The components that are similar to those in the first exemplary embodiment are respectively given the same reference numerals.

The casing 7 of the imaging apparatus 140 includes a connection portion 9D.

The connection portion 9D continuously connects the bottom portion 72, the side portion 73 of the shorter side, and the side portion 73 of the longer side. The connection portion 9D includes a first connection portion 91D, a second connection portion 92D, and a third connection portion 93D. The first connection portion 91D is substantially parallel to the entrance portion 71 and the bottom portion 72. The second connection portion 92D is substantially parallel to the side portion 73 of the longer side, whereas the third connection portion 93D is substantially parallel to the side portion 73 of the shorter side.

The first connection portion 91D includes the window portion 13, and the wireless power reception portion 8 is arranged inside the window portion 13.

Figure 5C:
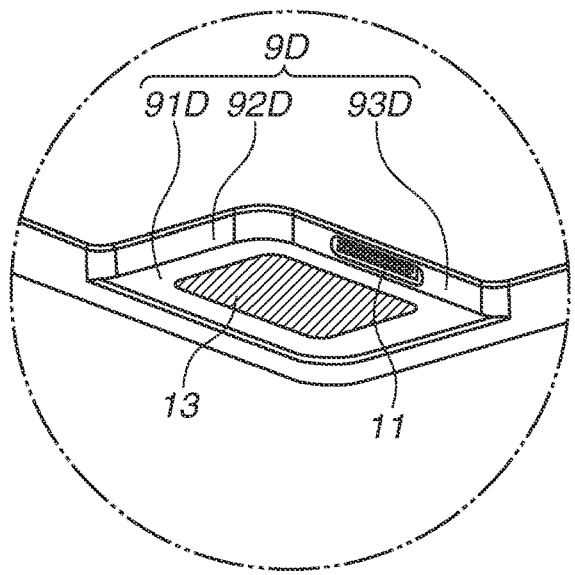

As illustrated in FIG. 5C, the connection portion 9D according to the present exemplary embodiment includes a connection terminal 11 as a connection portion that is electrically connected externally. More specifically, the connection terminal 11 is provided to the third connection portion 93D of the connection portion 9D. The connection terminal 11 functions as an interface during wired communication. Thus, the imaging apparatus 140 can receive not only power transferred wirelessly to the wireless power reception portion 8 but also power supplied through the wired connection from an external power supply via the connection terminal 11. The imaging apparatus 140 is wire connected with an external apparatus via the connection terminal 11 to thereby transmit and receive control signals and transfer radiographic images. A user can select whether to use the wired connection method or the wireless connection method to transfer power or information, depending on the situation.

There is a case in which the imaging apparatus 140 is formed to have an outer size specified by Japanese Industrial Standard (JIS) Z4905. Thus, it is required to effectively use the internal space of the casing 7. In the imaging apparatus 140 according to the present exemplary embodiment, the connection terminal 11 is arranged at the connection portion 9D on which the wireless power reception portion 8 is arranged. Thus, no new space for placing the connection terminal 11 is needed, which enables an effective use of the internal space of the casing 7 of the imaging apparatus 140.

An imaging apparatus 150 according to a third exemplary embodiment will be described with reference to FIGS. 6A, 6B, and 7.

Figure 6A:
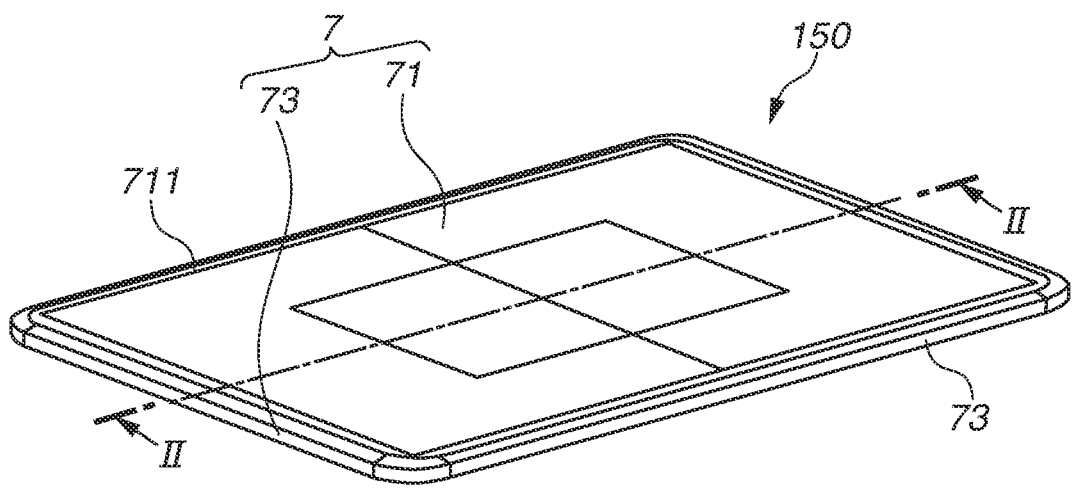
FIGS. 6A and 6B are external views illustrating an example of a radiographing apparatus according to a third exemplary embodiment.
Figure 6B:
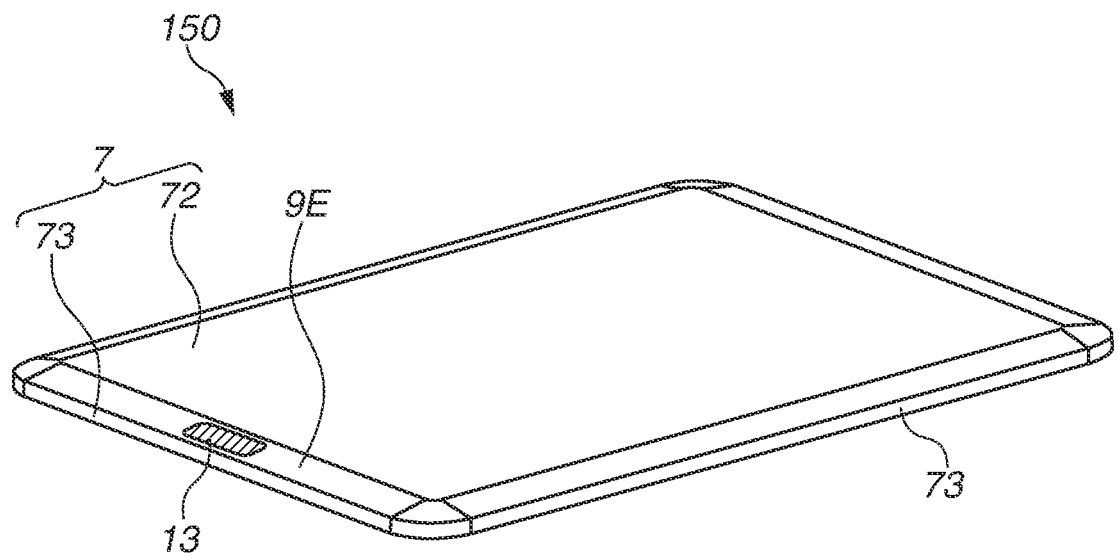
Figure 7:
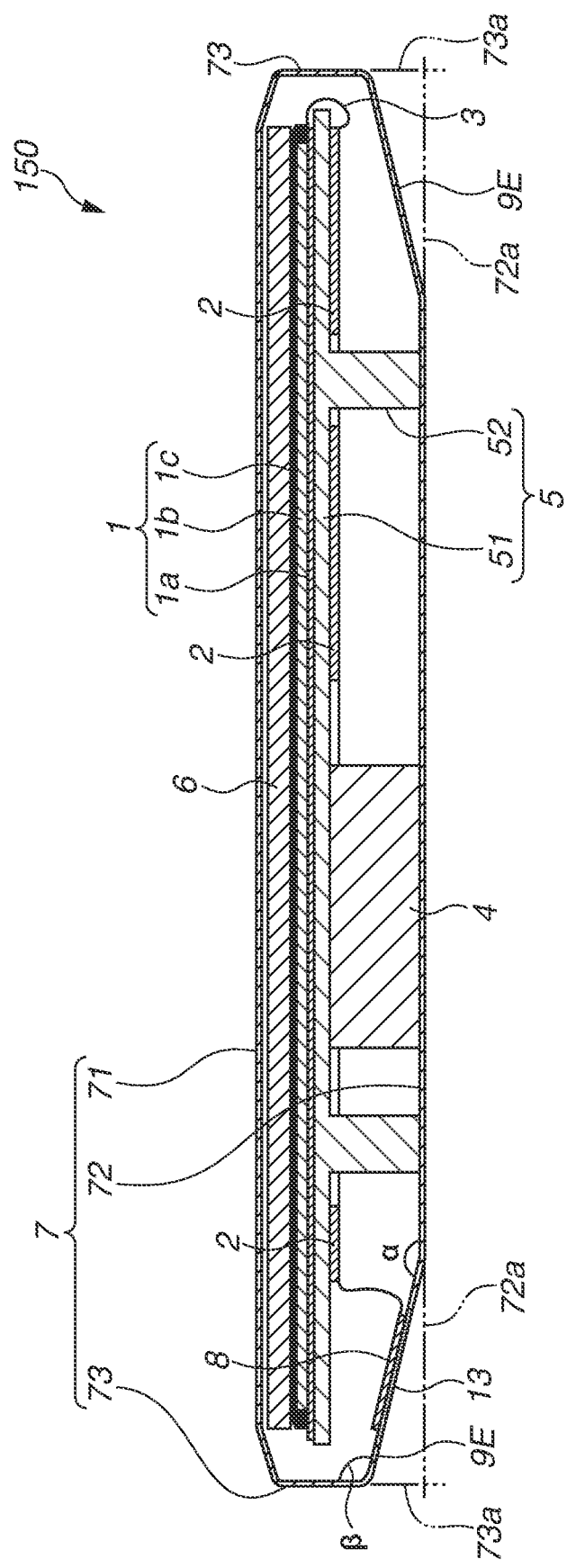
FIG. 7 is a cross-sectional view illustrating an example of the radiographing apparatus according to the third exemplary embodiment.

FIG. 6A is an external view illustrating the imaging apparatus 150 viewed from the radiation incident direction. FIG. 6B is an external view illustrating the imaging apparatus 150 viewed from the opposite side of the imaging apparatus 150 in FIG. 6A. FIG. 7 is a cross-sectional view illustrating a cross section that is cut along a line II-II in FIG. 6A and viewed from an arrow direction. The components that are similar to those in the first exemplary embodiment are respectively given the same reference numerals.

The casing 7 of the imaging apparatus 150 includes a connection portion 9E.

The connection portion 9E continuously connects the bottom portion 72 and the side portions 73. More specifically, the connection portion 9E is an example of an inclined portion and is inclined with respect to each of the bottom portion 72 and the side portions 73. The connection portion 9E is substantially plate-shaped with an externally exposed surface (outer surface) that is substantially flat. The connection portion 9E according to the present exemplary embodiment is continuously formed along the entire periphery of the casing 7. As illustrated in FIG. 7, an angle $\alpha$ on the casing 7 side between the bottom portion 72 and the connection portion 9E is larger than an angle $\beta$ on the casing 7 side between the side portion 73 and the connection portion 9E. Thus, the connection portion 9E is gently inclined with respect to the bottom portion 72. The angle $\alpha$ of the connection portion 9E with respect to the bottom portion 72 is desirably greater than 135 degrees and less than 180 degrees. The angle $\alpha$ is set to an angle greater than 135 degrees because an effective use of the internal space of the casing 7 is possible in the case in which the angle $\alpha$ is greater than 135 degrees. The angle $\alpha$ is set to an angle less than 180 degrees because if the angle $\alpha$ is 180 degrees, the connection portion 9E does not function as the connection portion 9E and becomes the bottom portion 72. The angle $\alpha$ of the connection portion 9E with respect to the bottom portion 72 can be less than or equal to 135 degrees.

The connection portion 9E includes the window portion 13, and the wireless power reception portion 8 is arranged inside the window portion 13. The wireless power reception portion 8 is arranged on a surface (inner surface) of the connection portion 9E that is not externally exposed. The wireless power reception portion 8 is arranged along the inner surface of the connection portion 9E, i.e., the wireless power reception portion 8 is arranged substantially parallel to the inner surface of the connection portion 9E. Since the inner surface of the connection portion 9E is inclined with respect to each of the bottom portion 72 and the side portion 73, the wireless power reception portion 8 arranged along the inner surface of the connection portion 9E is also inclined.

As described above, the connection portion 9E is inclined with respect to the bottom portion 72 and the side portion 73 to thereby prevent foreign matter and dust from remaining at the connection portion 9E. This prevents a decrease in the efficiency in power reception by the wireless power reception portion 8. The wireless power reception portion 8 is arranged inside the inclined connection portion 9E to enable an effective use of the internal space of the casing 7.

While the structure in which the connection portion 9E is continuously formed along the entire periphery of the casing 7 is described in the present exemplary embodiment, the structure is not limited to the above-described structure, and the connection portion 9E can be formed only on a portion of the side portion 73 including the side portion on which the wireless power reception portion 8 is arranged.

Figure 8A:
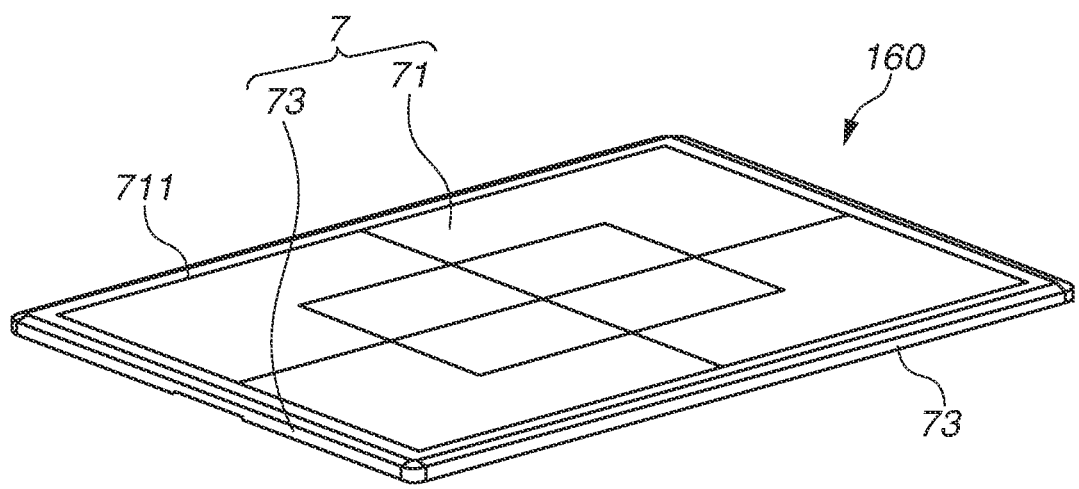
FIGS. 8A and 8B are external views illustrating an example of a radiographing apparatus according to a modified example of the third exemplary embodiment.
Figure 8B:
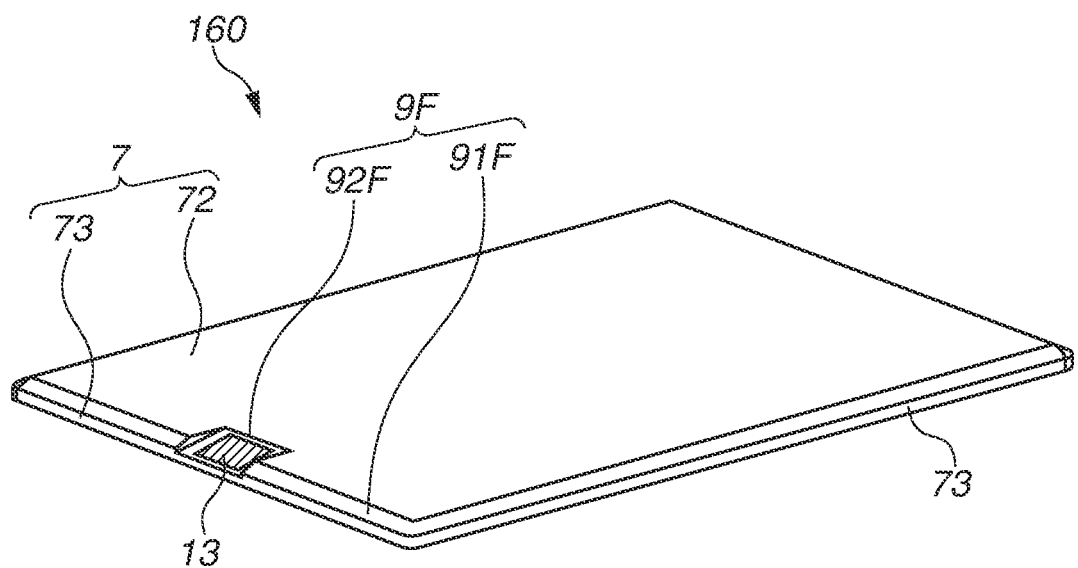

Next, an imaging apparatus 160 according to a first modified example of the third exemplary embodiment will be described with reference to FIGS. 8A and 8B. While the imaging apparatus 150 illustrated in FIGS. 6A, 6B, and 7 includes the connection portion 9E having a uniform shape around the casing 7, the imaging apparatus 160 illustrated in FIGS. 8A and 8B is different in the shape of a connection portion 9F on which the wireless power reception portion 8 is arranged. The components that are similar to those in FIGS. 6A, 6B, and 7 are given the same reference numerals.

FIG. 8A is an external view illustrating the imaging apparatus 160 viewed from the radiation incident direction. FIG. 8B is an external view illustrating the imaging apparatus 160 viewed from the opposite side of the imaging apparatus 160 in FIG. 8A.

As illustrated in FIG. 8B, the casing 7 of the imaging apparatus 160 includes the connection portion 9F.

The connection portion 9F includes a first connection portion 91F and a second connection portion 92F. Each of the first connection portion 91F and the second connection portion 92F is substantially plate-shaped with an externally exposed surface (outer surface) that is substantially flat. The first connection portion 91F and the second connection portion 92F are examples of an inclined portion.

The first connection portion 91F is continuously formed along the entire periphery of the casing 7 excluding the second connection portion 92F. The second connection portion 92F is formed at a portion of the casing 7. More specifically, the second connection portion 92F is formed at a substantially central portion of the side portion 73 of the shorter side of the casing 7. The second connection portion 92F is inclined with respect to the bottom portion 72 more gently than the first connection portion 91F. For example, as illustrated in FIG. 7, an angle α of the second connection portion 92F is greater than an angle α of the first connection portion 91F, where the angle α is an angle on the casing 7 side between the second connection portion 92F or the first connection portion 91F and the bottom portion 72. An angle β of the second connection portion 92F is less than an angle β of the first connection portion 91F, where the angle β is an angle on the casing 7 side between the second connection portion 92F or the first connection portion 91F and the side portion 73.

The second connection portion 92F includes the window portion 13, and the wireless power reception portion 8 is arranged inside the window portion 13. The wireless power reception portion 8 is arranged along the inner surface of the second connection portion 92F, i.e., wireless power reception portion 8 is arranged substantially parallel to the inner surface, as in FIG. 7. Since the inner surface of the second connection portion 92F is inclined with respect to each of the bottom portion 72 and the side portion 73, the wireless power reception portion 8 arranged along the inner surface of the second connection portion 92F is also inclined.

As described above, the second connection portion 92F on which the wireless power reception portion 8 is arranged is inclined with respect to the bottom portion 72 more gently than the first connection portion 91F to thereby increase the inner space of the casing 7.

While the structure in which the first connection portion 91F is included in the present modified example is described, the first connection portion 91F can be omitted. More specifically, the part of the entire periphery of the casing 7 other than the second connection portion 92F can be provided with no connection portion, and the bottom portion 72 and the side portions 73 can be continuous to each other.

Figure 9:
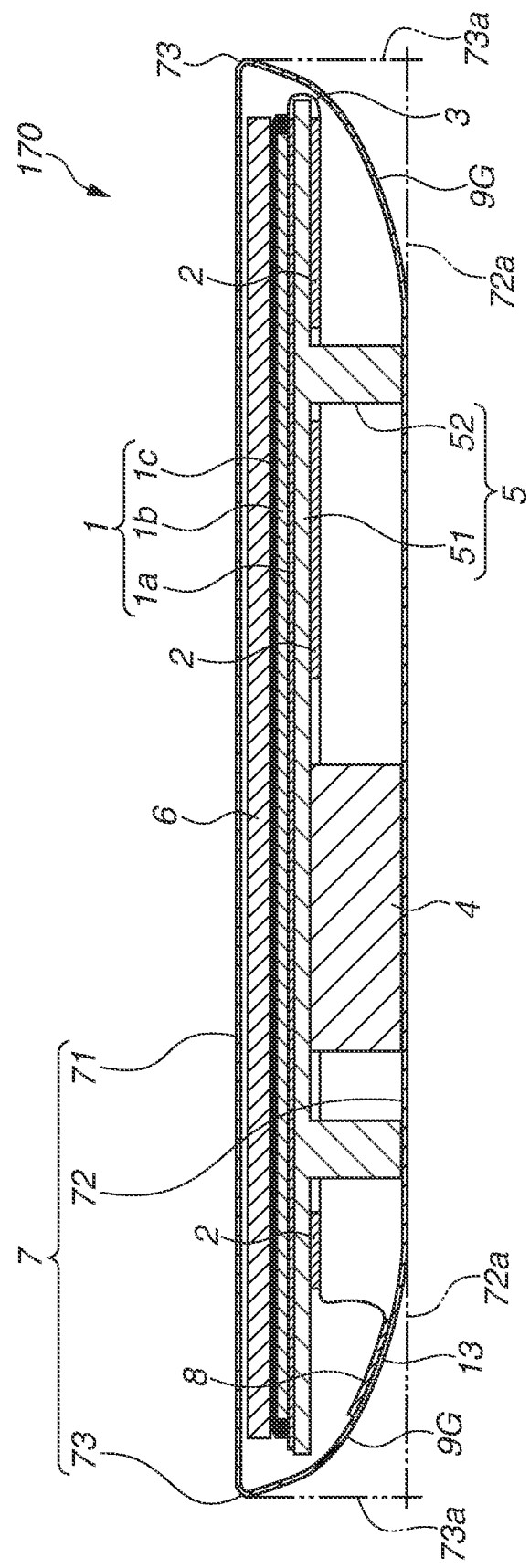
FIG. 9 is a cross-sectional view illustrating an example of a radiographing apparatus according to a modified example of the third exemplary embodiment.

Next, an imaging apparatus 170 according to a second modified example of the third exemplary embodiment will be described with reference to FIG. 9. While the casing 7 of the imaging apparatus 150 illustrated in FIGS. 6A, 6B, and 7 includes the connection portion 9E, which is substantially plate-shaped with an externally exposed surface (outer surface) that is substantially flat, the imaging apparatus 170 illustrated in FIG. 9 is different in the shape of a connection portion 9G on which the wireless power reception portion 8 is arranged. The components that are similar to those in FIGS. 6A, 6B, and 7 are respectively given the same reference numerals.

FIG. 9 is a cross-sectional view illustrating the imaging apparatus 170.

The casing 7 of the imaging apparatus 170 includes the connection portion 9G.

The connection portion 9G continuously connects the bottom portion 72 and the side portions 73. The side portions 73 according to the present modified example are portions of the casing 7 that are located at outermost positions. In the present modified example, the side portions 73 are located at outer edges of the entrance portion 71. The connection portion 9G is an example of an inclined portion and is inclined with respect to the bottom portion 72. The connection portion 9G is substantially plate-shaped with an externally exposed surface (outer surface) curved outward in a protruded manner. The connection portion 9G according to the present exemplary embodiment is continuously formed along the entire periphery of the casing 7.

The connection portion 9G includes the window portion 13, and the wireless power reception portion 8 is arranged inside the window portion 13. The wireless power reception portion 8 is arranged on a surface (inner surface) of the connection portion 9G that is not externally exposed. The wireless power reception portion 8 is arranged along the inner surface of the connection portion 9G, i.e., the wireless power reception portion 8 is arranged substantially parallel to the inner surface. Since the inner surface of the connection portion 9G is also curved similarly to the outer surface, the wireless power reception portion 8 arranged along the inner surface of the connection portion 9G is also curved. In this case, the wireless power reception portion 8 can be formed with a flexible circuit substrate.

As described above, the connection portion 9G is inclined to curve in a protrusion manner so that when the imaging apparatus 170 is brought into contact with a patient during imaging, the patient is less likely to have a strange feeling. The connection portion 9G is inclined to curve outward in a protrusion manner to thereby increase the internal space of the casing 7. The second extension plane 73a in FIG. 9 is a plane that is formed by extending the surface of the side portions 73 in a direction orthogonal to the entrance portion 71.

While the structure in which the side portions 73 are outer edges of the entrance portion 71 is described in the present modified example, the side portions 73 can be substantially plate-shaped as in the other exemplary embodiments/examples.

The imaging apparatus 100 according to a fourth exemplary embodiment will be described with reference to FIGS. 10A to 13B.

Figure 10A:
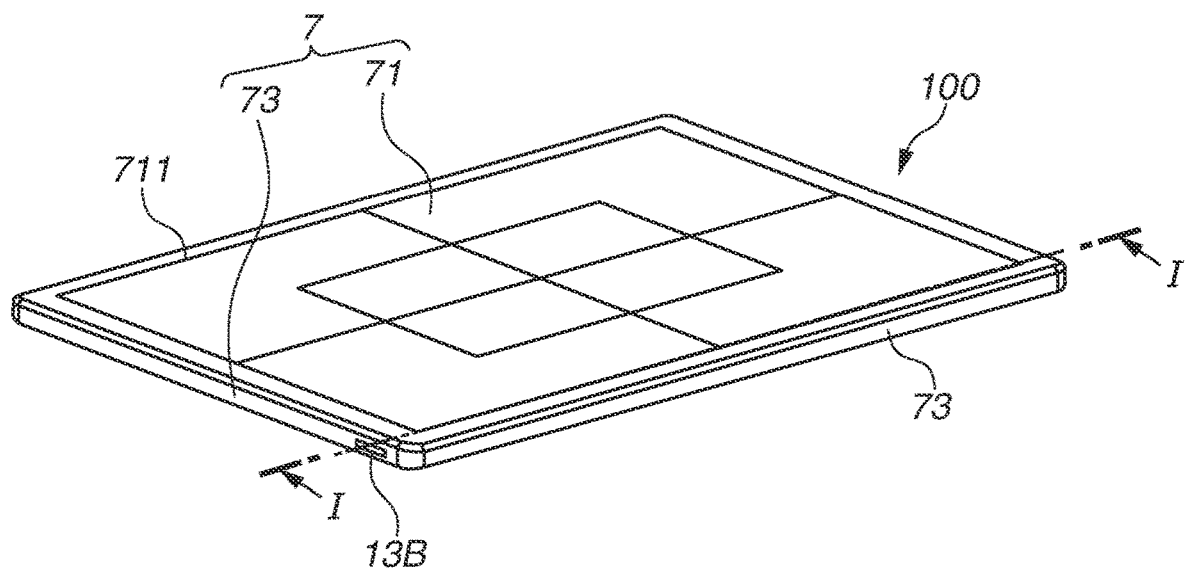
FIGS. 10A and 10B are external views illustrating an example of a radiographing apparatus according to a fourth exemplary embodiment.
Figure 10B:
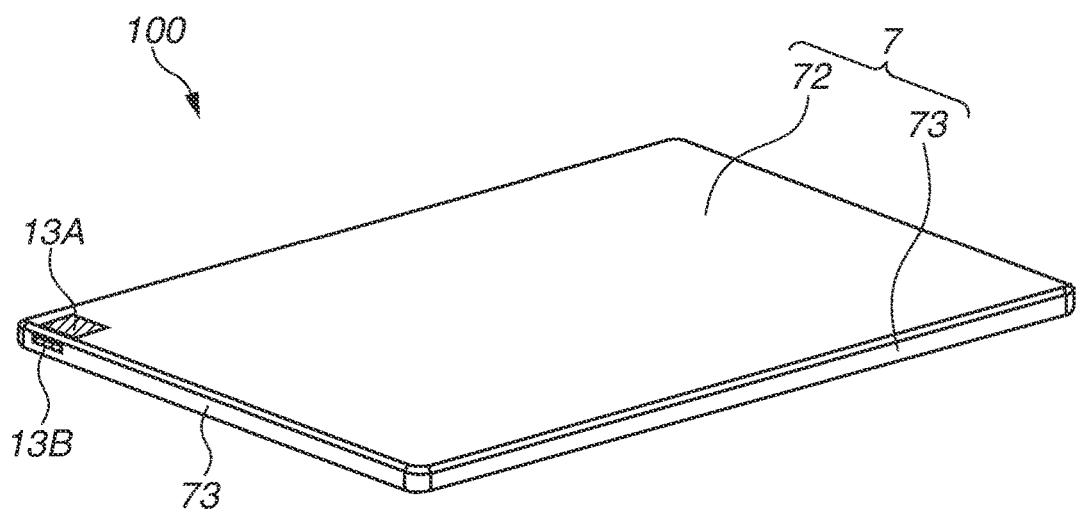
Figure 11A:
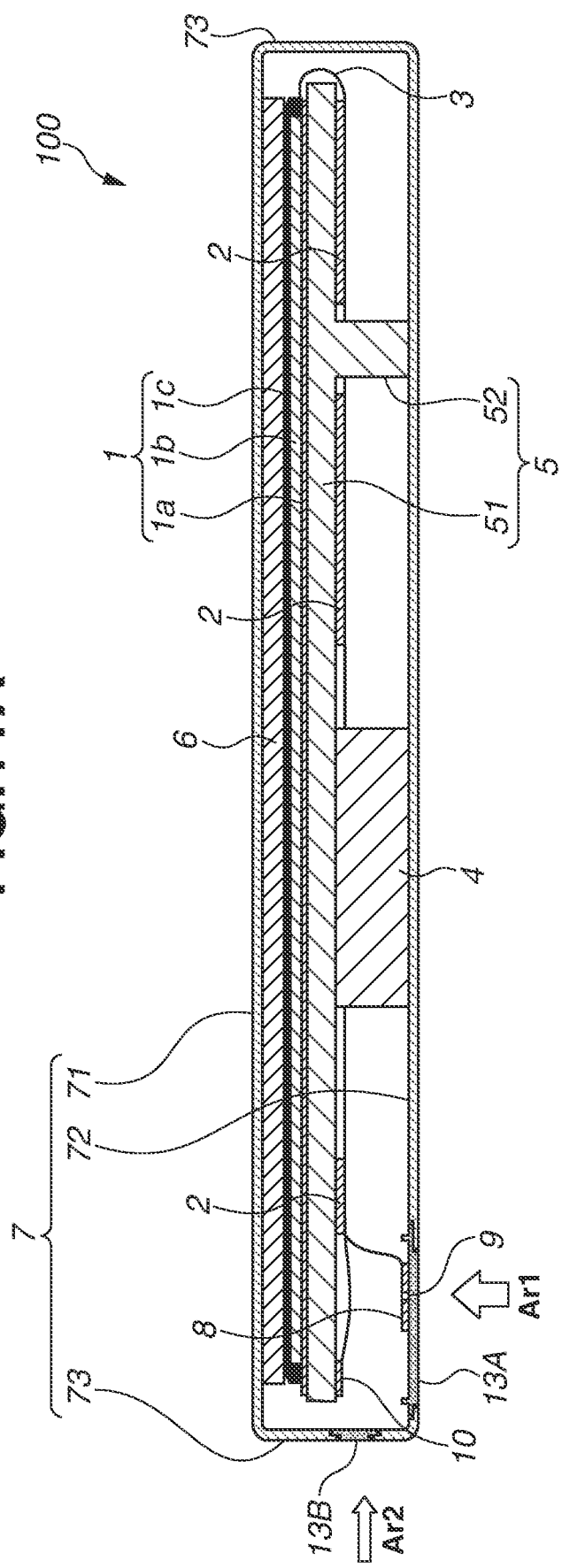
FIGS. 11A, 11B, and 11C respectively are a cross-sectional view, external view, and enlarged view illustrating an example of the radiographing apparatus according to the fourth exemplary embodiment.
Figure 11B:
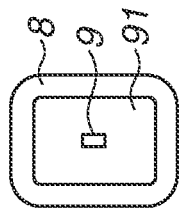
Figure 11C:
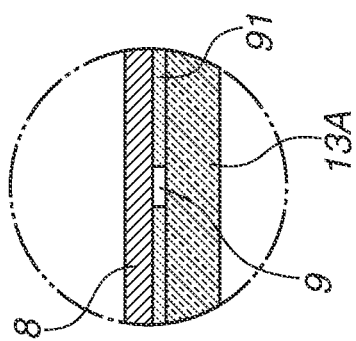

FIG. 10A is an external view illustrating the imaging apparatus 100 viewed from the radiation incident direction. FIG. 10B is an external view illustrating the imaging apparatus 100 viewed from the opposite side of the imaging apparatus 100 illustrated in FIG. 10A. FIG. 11A is a cross-sectional view illustrating a cross section cut along a line I-I in FIG. 10A and viewed from an arrow direction. FIG. 11B is an external view illustrating the wireless power reception portion 8 and a light-emitting diode (LED) 9 viewed from the direction of an arrow Ar1 in FIG. 11A. FIG. 11C is an enlarged view illustrating a portion around the LED 9 illustrated in FIG. 11A.

The power reception by the wireless power reception portion 8 is controlled by the control substrate 2.

The LED 9 functions as an indicator for indicating a state of the imaging apparatus 100. For example, the LED 9 emits light to indicate an activation state or operation state of the imaging apparatus 100 for a user. The LED 9 is an example of a light source.

An antenna 10 wirelessly transmits and receives data to and from an external apparatus. The control substrate 2 controls the data transmission and reception between the antenna 10 and the external apparatus. The antenna 10 is an example of a wireless transmission/reception unit or wireless data transmission unit.

In a case in which the casing 7 is made of a conductive material, the power reception by the wireless power reception portion 8 and the data transfer by the antenna 10 are less efficient. In a case in which the casing 7 is made of a material that does not transmit light, a user cannot recognize the light of the LED 9. Thus, a window portion can be formed in the casing 7 to increase data, power, and light transmission efficiencies. Forming a window portion requires a hole to be formed at a portion of the casing 7, and this causes the structure of the imaging apparatus 100 to become discontinuous, and concentrated stress is likely to occur in the vicinity of the window portion. Since the rigidity of the casing 7 decreases, the strength of the imaging apparatus 100 also decreases. The imaging apparatus 100 is required to have a sufficient strength not to be damaged by impact force and external force that are likely to be applied to the imaging apparatus 100 during imaging.

The casing 7 according to the present exemplary embodiment has a structure that can prevent a decrease in strength caused by a window portion.

As illustrated in FIGS. 10A, 10B, 11A, 11B, and 11C, the casing 7 includes two window portions 13A and 13B. The window portions 13A and 13B are arranged near one of the four corner portions of the rectangular shape of the casing 7. More specifically, the window portion 13A is arranged at the bottom portion 72, whereas the window portion 13B is arranged at the side portion 73 of the shorter side. The window portions 13A and 13B are arranged at the same position in the direction along the shorter sides of the casing 7, or at a position at which the window portions 13A and 13B overlap in the direction along the shorter sides of the casing 7. The window portion 13A is continuous to the bottom portion 72 and has substantially a plate-shape and is substantially parallel to the bottom portion 72. The window portion 13B is continuous to the side portions 73 and has substantially a plate-shape and is substantially parallel to the side portions 73.

As illustrated in FIGS. 11A and 11C, the wireless power reception portion 8, the LED 9, and the antenna 10 are arranged inside the window portion 13A. The wireless power reception portion 8, the LED 9, and the antenna 10 are arranged in an overlapped manner with respect to the window portion 13A when viewed from the arrow Ar1 direction specified in FIG. 11A. In other words, the wireless power reception portion 8, the LED 9, and the antenna 10 are arranged in an overlapped manner with respect to the window portion 13A when viewed from the direction that is orthogonal to the outer surface of the window portion 13A. More specifically, the wireless power reception portion 8 and the LED 9 are arranged along the inner surface of the window portion 13A, and the antenna 10 is arranged at a position apart from the inner surface of the window portion 13A. Thus, the window portion 13A has a function of a window portion for the power reception by the wireless power reception portion 8, a function of a window portion for the transmission of the light of the LED 9, and a function of a window portion for the data transfer by the antenna 10. The window portion 13A functions mainly as a window portion for the wireless power reception portion 8 and the LED 9, as the wireless power reception portion 8 and the LED 9 are arranged in contact with the inner surface.

The antenna 10 is arranged inside the window portion 13B. The antenna 10 is arranged to overlap the window portion 13B when viewed from an arrow Ar2 direction in FIG. 11A. In other words, the antenna 10 is arranged to overlap the window portion 13B when viewed from the direction orthogonal to the outer surface of the window portion 13B. More specifically, the antenna 10 is arranged at a position apart from the inner surface of the window portion 13B. Thus, the window portion 13B has the function of the window portion for the data transfer by the antenna 10.

In the present exemplary embodiment, the wireless power reception portion 8 and the LED 9 are arranged in an overlapped manner. More specifically, the LED 9 is arranged between the wireless power reception portion 8 and the inner surface of the window portion 13A.

FIG. 11B illustrates a structure of the wireless power reception portion 8 and the LED 9 viewed from the arrow Ar1 direction in FIG. 11A. The LED 9 is arranged at a substantially central portion of the wireless power reception portion 8. The wireless power reception portion 8 is larger than a substrate 91 on which the LED 9 is mounted, and the wireless power reception portion 8 is arranged inside the window portion 13A to cover the substrate 91 from the inside of the casing 7. The wireless power reception portion 8 and the LED 9 have the above-described structure so that the single window portion 13A is shared as the window portions of the wireless power reception portion 8 and the LED 9 and the size of the window portion 13A is reduced. This prevents a decrease in strength of the casing 7. The wireless power reception portion 8 and the LED 9 are arranged as described above so that the space is reduced and thus the size of the imaging apparatus 100 is reduced, compared to a case in which the wireless power reception portion 8 and the LED 9 are separately arranged.

The antenna 10 is supported by an opposite surface of the substrate support portion 51, to the surface supporting the detection panel 1. The antenna 10 is arranged not to overlap the wireless power reception portion 8 and the LED 9 when viewed from the arrow Ar1 direction. The antenna 10 is arranged inside the window portions 13A and 13B. Thus, data is transferred through the two window portions 13A and 13B, whereby a radiation range of the antenna 10 increases.

In a case in which sufficient radiation characteristics of the antenna 10 are obtained only with the window portion 13A, the casing 7 does not need the window portion 13B. In this case, the window portion 13A is shared as the window portions of the wireless power reception portion 8, the LED 9, and the antenna 10. This further prevents a decrease in strength of the casing 7.

In the present exemplary embodiment, at least part of the window portion 13A is made of a light-transmissive material so that a user can visually recognize the light of the LED 9. For example, resin or fiber-reinforced resin is used as a material of the window portion 13A, and the window portion 13A is entirely or partially formed as a light transmission portion.

In a case of forming the window portion 13A partially as a light transmission portion, a light-transmissive material and a non-light-transmissive material are integrally molded by multi-material molding. Alternatively, a light-transmissive material and a non-light-transmissive material can be molded separately and then joined together using an adhesive, industrial tape, or ultrasonic welding.

In a case in which the window portion 13A is entirely formed as a light-transmissive material, the outer or inner surface of the window portion 13A is painted or printed or a light-shielding sheet is placed on the outer or inner surface to thereby prevent transmission at an undesired position or adjust the amount of light to be transmitted.

The window portion 13B does not function as a window portion of the LED 9. Thus, the window portion 13B does not have to be made of a light-transmissive material, and at least part of the window portion 13B only needs to be made of a non-conductive material.

The window portions 13A and 13B are formed to have a thickness suitable to prevent a significant decrease in power/data transfer efficiency. The window portion 13A is formed to have a thickness suitable for transmitting the light of the LED 9.

In order to provide the casing 7 with the window portions 13A and 13B, the window portions 13A and 13B are joined to the casing 7 using an adhesive or industrial tape or are fastened with a screw to the casing 7. At this time, waterproof packing can be provided between the window portions 13A and 13B and the casing 7 or the window portions 13A and 13B can be attached with a waterproof double-sided tape to thereby be able to increase water-resistance. The casing 7 can be formed by integrally molding the casing 7 and the window portions 13A and 13B using outsert molding or multi-material molding. Integrally molding the casing 7 and the window portions 13A and 13B can increase the interfacial strength between the casing 7a and the window portions 13A and 13B, and thus the strength of the imaging apparatus 100 can increase.

As described above, the wireless power reception portion 8 and the LED 9 are arranged in contact with the inner surface of the single window portion 13A, whereby the single window portion 13A is shared as the window portions of the wireless power reception portion 8 and the LED 9 to thereby reduce the number of window portions to be provided to the casing 7. The wireless power reception portion 8, the LED 9, and the antenna 10 are arranged inside the single window portion 13A so that the single window portion 13A is shared as the window portions of the wireless power reception portion 8, the LED 9, and the antenna 10 to thereby reduce the number of window portions to be provided to the casing 7. This prevents a decrease in strength of the casing 7. The wireless power reception portion 8 is arranged to overlap the window portion 13A when viewed from the direction orthogonal to the outer surface of the window portion 13A, whereby the efficiency in power reception by the wireless power reception portion 8 can increase. Similarly, the LED 9 is arranged to overlap the window portion 13A to thereby increase the visibility of the LED 9. Similarly, the antenna 10 is arranged to overlap the window portion 13A to thereby increase the efficiency in data transfer by the antenna 10.

While the structure in which the wireless power reception portion 8, the LED 9, and the antenna 10 are arranged at the single window portion 13A is described according to the present exemplary embodiment, the structure is not limited to the above-described structure, and the wireless power reception portion 8 and one of the LED 9 and the antenna 10 can be arranged at the single window portion 13A.

Next, an imaging apparatus 100 according to a modified example of the fourth exemplary embodiment will be described with reference to FIGS. 12A, 12B, 13A, and 13B. While the imaging apparatus 100 illustrated in FIGS. 10A, 10B, 11A, 11B, and 11C includes the window portion 13A at the bottom portion 72 and the window portion 13B at the side portion 73, the imaging apparatus 100 illustrated in FIGS. 12A, 12B, 13A, and 13B includes the window portion 13C at an inclined portion 74. The components that are similar to those in FIGS. 10A, 10B, 11A, 11B, and 11C are respectively given the same reference numerals.

Figure 12A:
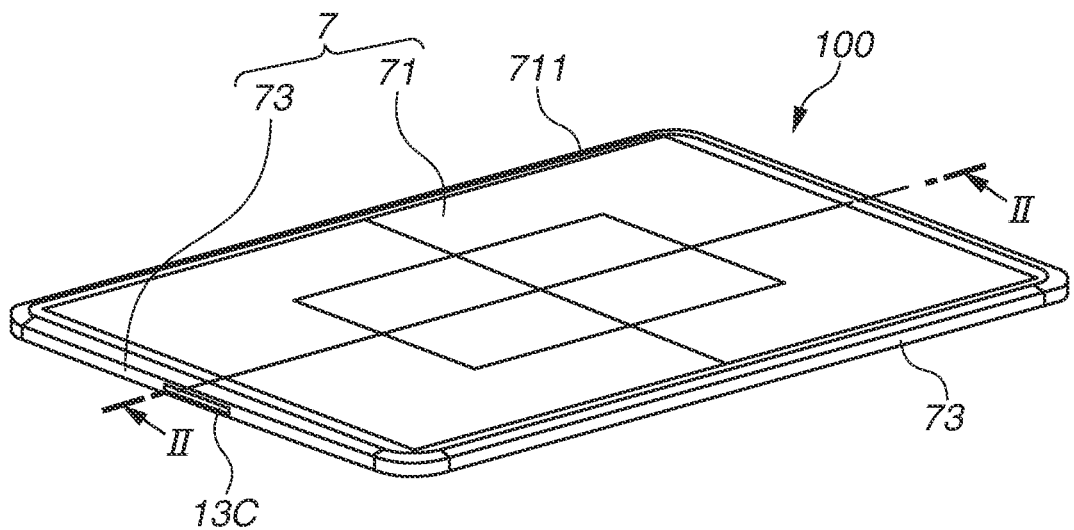
FIGS. 12A and 12B are external views illustrating an example of a radiographing apparatus according to a modified example of the fourth exemplary embodiment.
Figure 12B:
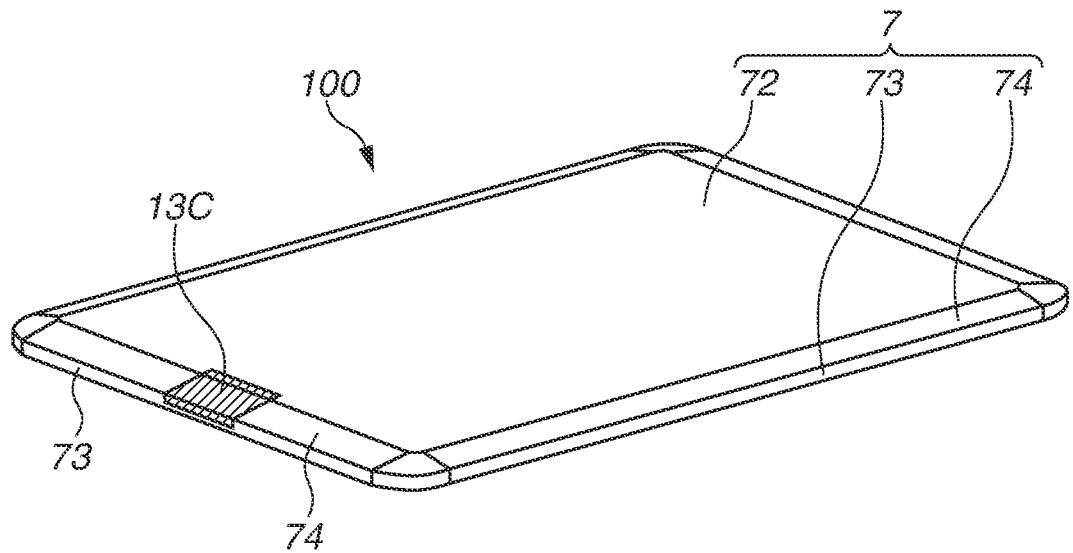

FIG. 12A is an external view illustrating the imaging apparatus 100 viewed from the radiation incident direction. FIG. 12B is an external view illustrating the imaging apparatus 100 viewed from the opposite side of the imaging apparatus 100 in FIG. 12A. FIG. 13A is a cross-sectional view illustrating a cross section cut along a line II-II in FIG. 12A and viewed from an arrow direction. FIG. 13B is an enlarged view illustrating a portion around the LED 9 illustrated in FIG. 13A.

The casing 7 of the imaging apparatus 100 according to the present exemplary embodiment includes the inclined portion 74 between the bottom portion 72 and the side portion 73. The inclined portion 74 functions as a connection portion that continuously connects the bottom portion 72 and the side portion 73. As used herein, the phrase "continuously connects" indicates that neither the bottom portion 72 nor the side portions 73 exist between the bottom portion 72 and the side portions 73.

The inclined portion 74 is inclined with respect to the bottom portion 72 and the side portion 73. The inclined portion 74 is continuously formed along a substantially entire periphery of the casing 7. As illustrated in FIG. 13A, the inclined portion 74 is substantially plate-shaped with an externally exposed surface (outer surface) that is substantially flat.

The casing 7 according to the present exemplary embodiment includes one window portion 13C. The window portion 13C is arranged on a shorter side of the rectangular shape of the casing 7 and at a substantially central portion of the shorter side in the direction along the shorter side. The window portion 13C is formed over the bottom portion 72 and the side portion 73 of the casing 7. More specifically, the window portion 13C includes a first portion 111C, which is continuous to the inclined portion 74, substantially parallel to the inclined portion 74, and substantially plate-shaped. Further, the window portion 13C includes a second portion 112C and a third portion 113C. The second portion 112C is formed continuous to the bottom portion 72, substantially parallel to the bottom portion 72, and substantially plate-shaped. The third portion 113C is formed continuous to the side portion 73, substantially parallel to the side portion 73, and substantially plate-shaped.

The wireless power reception portion 8, the LED 9, and the antenna 10 are arranged inside the window portion 13C. The wireless power reception portion 8, the LED 9, and the antenna 10 are arranged in an overlapped manner with respect to the window portion 13C when viewed from either one of the arrow Ar1 direction and the arrow Ar2 direction. The wireless power reception portion 8 and the LED 9 are arranged in an overlapped manner with respect to the first portion 111C when viewed from the direction orthogonal to the outer surface of the first portion 111C. The antenna 10 is arranged in an overlapped manner with respect to the second portion 112C when viewed from the direction orthogonal to the outer surface of the second portion 112C. More specifically, the wireless power reception portion 8 and the LED 9 are arranged along the inner surface of the first portion 111C, and the antenna 10 is arranged along the inner surface of the second portion 112C. Thus, the window portion 13C has the functions as the window portions for the wireless power reception portion 8, the LED 9, the antenna 10. As in FIG. 2 described above, the wireless power reception portion 8 and the LED 9 overlap each other.

As described above, the wireless power reception portion 8, the LED 9, and the antenna 10 are arranged at the single window portion 13C so that the single window portion 13C is shared as the window portions of the wireless power reception portion 8, the LED 9, and the antenna 10 to thereby reduce the number of window portions to be provided to the casing 7. This prevents a decrease in strength of the casing 7. Since the window portion 13C is arranged over the bottom portion 72 and the side portion 73, the wireless power reception portion 8 can widely receive power and the visibility of the LED 9 and radiation characteristics of the antenna 10 increase, compared to the case in which the window portion 13C is formed only at the bottom portion 72 or the side portion 73.

While the structure in which the wireless power reception portion 8 and the LED 9 overlap each other is described in the present exemplary embodiment, the structure is not limited to the above-described structure. For example, the wireless power reception portion 8 and the antenna 10 can overlap, the LED 9 and the antenna 10 can overlap, or all the wireless power reception portion 8, the LED 9, and the antenna 10 can overlap. This structure enables space reduction, and the sizes of the window portions 13A, 13B, and 13C can be further reduced.

While the structure in which the window portion 13C includes the first portion 111C is described in the modified example described above, the structure is not limited to the above-described structure, and the second portion 112C and the third portion 113C can be formed continuously without the first portion 111C.

In the present exemplary embodiment, in a case in which the wireless power reception portion 8 and the antenna 10 are located close to each other, operations of the wireless power reception portion 8 and the antenna 10 can interfere to cause a malfunction. Thus, a method for preventing interference as described below can be applied.

First, the imaging apparatus 100 or 110 sets a frequency band for use in wireless power reception by the wireless power reception portion 8 and a frequency band for use in wireless data transfer by the antenna 10 such that the set frequency bands are different from each other. By setting the frequency bands for the wireless power reception portion 8 and the antenna 10 to different frequency bands in this way, it is possible to prevent interference between the operations of the wireless power reception portion 8 and the antenna 10.

Second, the control substrate 2 of the imaging apparatus 100 or 110 performs control such that the wireless power reception portion 8 and the antenna 10 do not operate simultaneously and the period of wireless power reception and the period of data transfer by the antenna 10 do not overlap. More specifically, the control substrate 2 performs control such that the wireless power reception portion 8 does not wirelessly receive power while the antenna 10 transfers data to an external device. The control substrate 2 performs control such that the wireless power reception portion 8 wirelessly receives power only while the antenna 10 does not transfer data. The control substrate 2 performs control to not operate the power reception portion 8 and the antenna 10 simultaneously as described above to thereby prevent interference between the operations of the wireless power reception portion 8 and the antenna 10. This enables stable data transfer and increasing the efficiency of wireless power reception.

An imaging apparatus 1120 according to a fifth exemplary embodiment will be described with reference to FIGS. 14A and 14B.

FIG. 14A is a cross-sectional view illustrating the imaging apparatus 1120. FIG. 14B is an enlarged view illustrating a portion around the LED 9 illustrated in FIG. 14A. The components that are similar to those in the fourth exemplary embodiment are respectively given the same reference numerals.

The imaging apparatus 1120 includes a light shielding sheet 12 arranged between the LED 9 and the detection panel 1. The light shielding sheet 12 corresponds to an example of a light shielding layer. The light shielding sheet 12 is larger than the wireless power reception portion 8 and is arranged inside the window portion 13A so as to cover the wireless power reception portion 8 from the inside of the casing 7. Since the LED 9 is arranged between the wireless power reception portion 8 and the inner surface of the window portion 13A, the light shielding sheet 12 covers the LED 9 from the inside of the casing 7 via the wireless power reception portion 8.

The light shielding sheet 12 shields the light of the LED 9 to prevent the light from reaching the detection panel 1. As described above, radiation incident on the detection panel 1 causes the phosphor layer 1b to emit light, and the emitted light is converted into an electric signal by the photoelectric conversion elements on the sensor substrate 1a. Thus, if the light of the LED 9 enters from the periphery of the detection panel 1, the light can have an unintended effect on a radiographic image.

The light shielding sheet 12 is arranged between the LED 9 and the detection panel 1 to thereby prevent the light of the LED 9 from reaching the detection panel 1. Since the light shielding sheet 12 is arranged inside the window portion 13A, a region of the window portion 13A where the light shielding sheet 12 is arranged does not allow external light to transmit and prevents light leakage.

The light shielding sheet 12 can be a magnetic sheet. Use of a magnetic sheet as the light shielding sheet 12 makes it possible to change a portion of a magnetic field generated during wireless power reception to a magnetic field direction along the magnetic sheet, whereby the magnetic field is prevented from entering the imaging apparatus 100. In a case in which the imaging apparatus 100 includes a metal material, an effect of a repulsive magnetic field that is generated by the metal material and repulses the magnetic field during wireless power reception, is reduced. As a result, the efficiency of wireless power reception can be increased. An effect of the magnetic field on the detection panel 1 and the control substrate 2 can be reduced to thereby reduce noise in a radiographic image.

The imaging apparatus 130 according to a sixth exemplary embodiment will be described with reference to FIGS. 15A, 15B, 16A, and 16B.

Figure 15A:
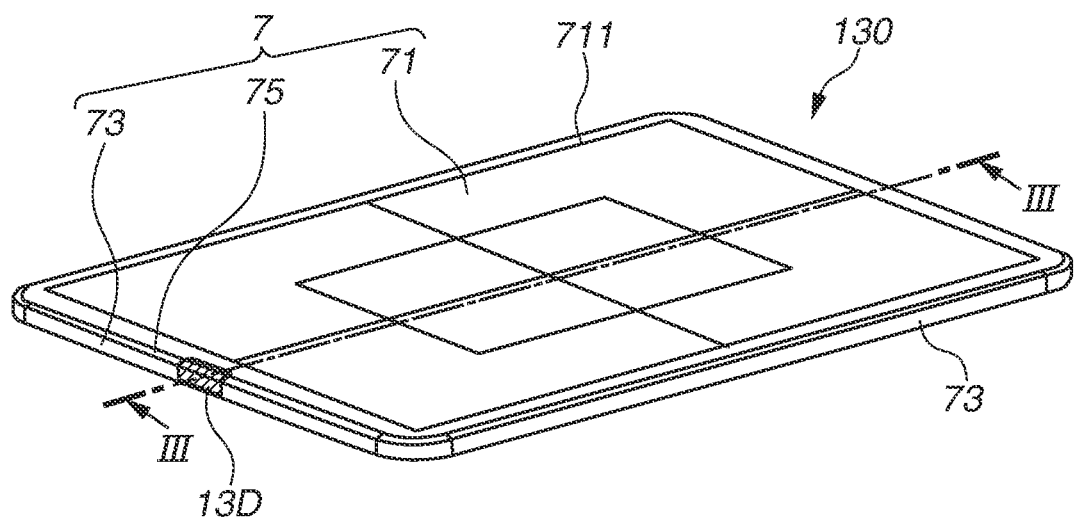
FIGS. 15A and 15B are external views illustrating an example of a radiographing apparatus according to a sixth exemplary embodiment.
Figure 15B:
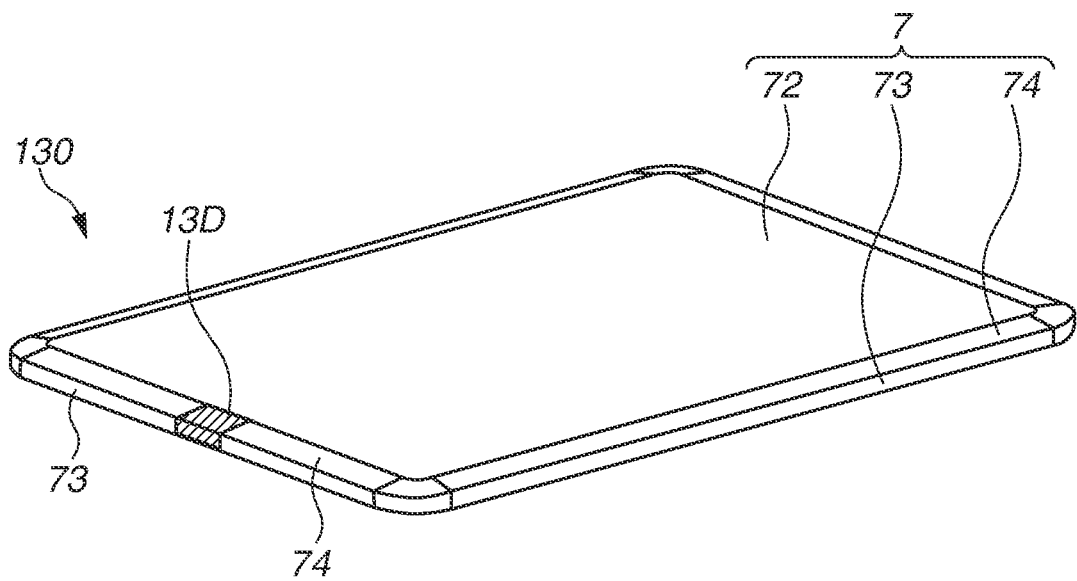

FIG. 15A is an external view illustrating the imaging apparatus 130 viewed from the radiation incident direction. FIG. 15B is an external view illustrating the imaging apparatus 130 viewed from the opposite side of the imaging apparatus 130 in FIG. 15A. FIG. 16A is a cross-sectional view illustrating a cross section cut along a line I-III in FIG. 16A and viewed from an arrow direction. FIG. 16B is an enlarged view illustrating a portion around the LED 9 illustrated in FIG. 16A. The components that are similar to those in the first exemplary embodiment are respectively given the same reference numerals.

The casing 7 of the imaging apparatus 130 according to the present exemplary embodiment includes a first inclined portion 74 and a second inclined portion 75.

The first inclined portion 74 is arranged between the bottom portion 72 and the side portions 73. The first inclined portion 74 functions as a connection portion that continuously connects the bottom portion 72 and the side portions 73. The first inclined portion 74 is inclined with respect to the bottom portion 72 and the side portions 73. The first inclined portion 74 is substantially plate-shaped with an externally exposed surface (outer surface) that is substantially flat.

The second inclined portion 75 is arranged between the entrance portion 71 and the side portions 73. The second inclined portion 75 functions as a connection portion that continuously connects the entrance portion 71 and the side portions 73. The second inclined portion 75 is inclined with respect to the entrance portion 71 and the side portions 73. The second inclined portion 75 is substantially plate-shaped with an externally exposed surface (outer surface) that is substantially flat.

The first inclined portion 74 and the second inclined portion 75 are continuously formed along the substantially entire periphery of the casing 7.

The casing 7 according to the present exemplary embodiment includes one window portion 13D. The window portion 13D is arranged at the shorter side of the rectangular shape of the casing 7 and at the substantially central portion of the shorter side in the direction along the shorter side. The window portion 13D is formed over the entrance portion 71 and the bottom portion 72 of the casing 7. More specifically, the window portion 13D includes a first portion 111D that is continuous to the side portions 73, substantially parallel to the side portions 73, and substantially plate-shaped. Further, the window portion 13D includes a second portion 112D and a third portion 113D. The second portion 112D is continuous to the first inclined portion 74, substantially parallel to the first inclined portion 74, and substantially plate-shaped. The third portion 113D is continuous to the second inclined portion 75, substantially parallel to the second inclined portion 75, and substantially plate-shaped. The window portion 13D includes a support portion 114D.

The wireless power reception portion 8, the LED 9, and the antenna 10 are arranged inside the window portion 13D. The wireless power reception portion 8, the LED 9, and the antenna 10 are arranged to overlap the window portion 13D when viewed from either one of the arrow Ar1 direction and the arrow Ar2 direction. The wireless power reception portion 8 and the LED 9 are arranged to overlap the first portion 111D when viewed from the direction that is orthogonal to the outer surface of the first portion 111D. The antenna 10 is arranged to overlap the second portion 112D when viewed from the direction orthogonal to the outer surface of the second portion 112D. More specifically, the wireless power reception portion 8 and the LED 9 are arranged along the inner surface of the first portion 111D, and the antenna 10 is arranged along the inner surface of the second portion 112D.

In the present exemplary embodiment, since the window portion 13D is arranged over the entrance portion 71 and the bottom portion 72, the window portion 13D is visible from various directions of the imaging apparatus 130. This increases the visibility of the LED 9 that functions as an indicator. The wireless power reception portion 8 can widely receive power and the radiation characteristics of the antenna 10 can be increased.

In contrast, since the window portion 13D is arranged over the entrance portion 71 and the bottom portion 72, the size of the window portion 13D is increased, and the strength of the window portion 13D can decrease. The support portion 114D of the window portion 13D according to the present exemplary embodiment is arranged between the inner surface of the second portion 112D and the inner surface of the third portion 113D. The support portion 114D is, for example, substantially pillar-shaped or substantially plate-shaped. As described above, the support portion 114D is included in the window portion 13D to thereby increase the rigidity of the window portion 13D and prevent a decrease in strength of the window portion 13D.

The support portion 114D is arranged between the LED 9 and the detection panel 1. Thus, the support portion 114D is substantially plate-shaped and formed to have a light-shielding property to thereby shield the light of the LED 9 so that the light does not reach the detection panel 1.

Next, an imaging system 140 will be described.

Figure 17:
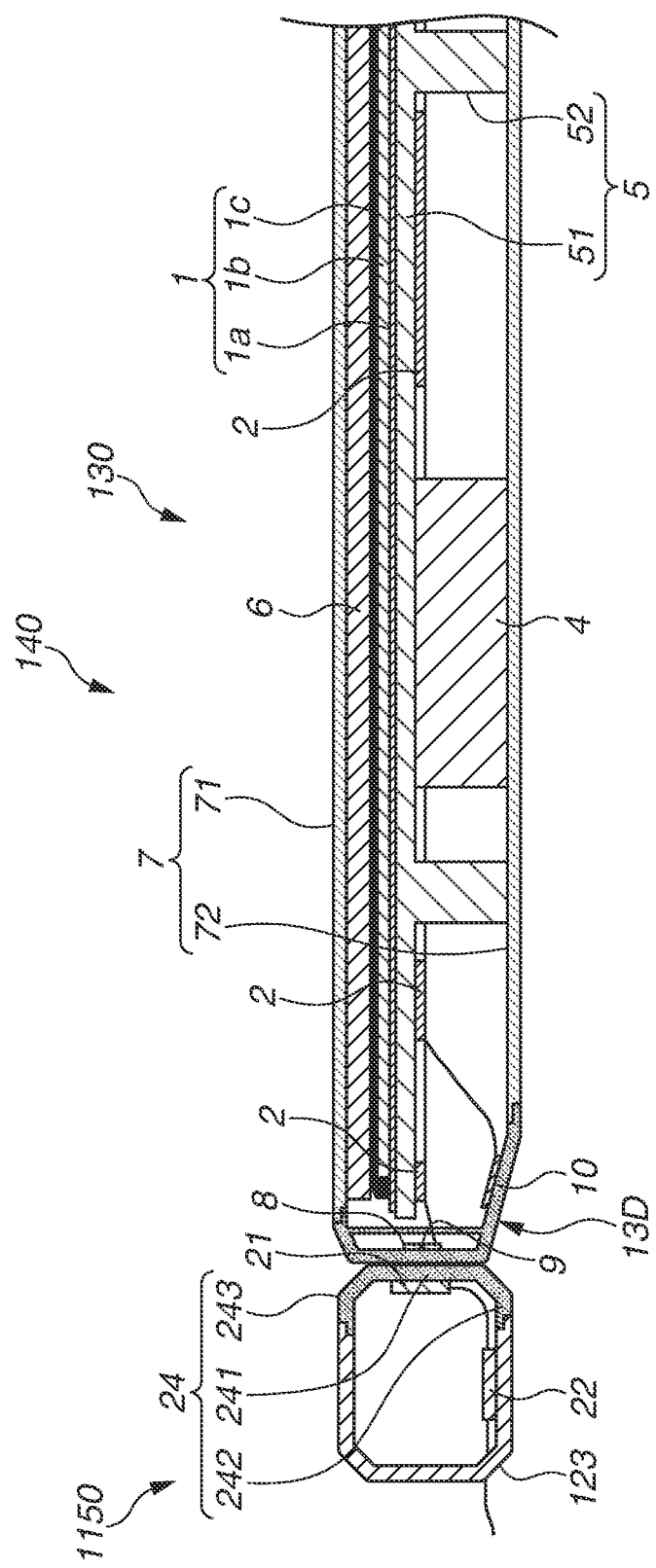
FIG. 17 is a cross-sectional view illustrating an example of a radiographing system according to the sixth exemplary embodiment.

FIG. 17 is a cross-sectional view illustrating a structure of the imaging system 140.

The imaging system 140 includes the imaging apparatus 130 and a wireless power transmission unit 1150. The structure of the imaging apparatus 130 is similar to the above-described structure, and the same reference numerals are respectively given to the similar components thereof.

The wireless power transmission unit 1150 wirelessly transmits power to the wireless power reception portion 8. The wireless power transmission unit 1150 includes the wireless power transmission portion 21, the control substrate 22, and a casing 123.

External power is supplied to the wireless power transmission portion 21 so that the wireless power transmission portion 21 transmits power to the wireless power reception portion 8. The control substrate 22 controls the wireless power transmission portion 21. The casing 123 encloses the components of the wireless power transmission unit 1150.

In the present exemplary embodiment, in a case of conducting wireless charging, the wireless power transmission unit 1150 is arranged near the window portion 13D of the casing 7 of the imaging apparatus 130 so that the wireless power transmission portion 21 and the wireless power reception portion 8 face each other. In this case, the window portion 13D of the imaging apparatus 130 is covered by the wireless power transmission unit 1150, and a user may not be able to visually recognize the light of the LED 9.

At least a portion of the casing 123 of the wireless power transmission unit 1150 according to the present exemplary embodiment that covers the window portion 13D of the casing 7 of the imaging apparatus 130 includes a light transmission portion 24. The light transmission portion 24 is substantially plate-shaped and is made of a light-transmissive material. The light transmission portion 24 includes a first transmission portion 241, a second transmission portion 242, and a third transmission portion 243. The wireless power transmission portion 21 is arranged inside the first transmission portion 241. The second transmission portion 242 and the third transmission portion 243 are continuous to the first transmission portion 241 and substantially orthogonal to the first transmission portion 241. Thus, a user can visually recognize the light of the LED 9 through the light transmission portion 24 even in a case in which the wireless power transmission unit 1150 is arranged near the window portion 13D of the casing 7 of the imaging apparatus 130 in order to conduct wireless charging.

In a case in which the window portion 13D of the casing 7 is covered by the wireless power transmission unit 1150 at the time of conducting wireless charging, a following method can be applied.

First, the control substrate 2 of the imaging apparatus 130 performs control in such a manner that the LED 9 does not emit light while the wireless power reception portion 8 wirelessly receives power. The LED 9 does not emit light to thereby reduce power consumption.

Second, the imaging apparatus 130 is formed to include a plurality of LEDs 9. The control substrate 2 of the imaging apparatus 130 performs control in such a manner that when the wireless power reception portion 8 wirelessly receives power, an LED 9 that is covered by the wireless power transmission unit 1150 does not emit light while an LED 9 that is visually recognizable by a user emits light. The LEDs 9 are controlled as described above so that a user can check the state of the imaging apparatus 130 and the power consumption is reduced.

While the structure in which the window portion 13D is formed over the entrance portion 71 and the bottom portion 72 of the casing 7 is described in the present exemplary embodiment, the structure is not limited to the above-described structure, and the window portion 13D can be formed over the side portions 73 and the entrance portion 71.

While the structure in which the second portion 112D is continuous to the first inclined portion 74 and substantially parallel to the first inclined portion 74 is described in the present exemplary embodiment, the structure is not limited to the above-described structure, and the second portion 112D can be continuous to the bottom portion 72 and substantially parallel to the bottom portion 72.

While the structure in which the third portion 113D is continuous to the second inclined portion 75 and substantially parallel to the second inclined portion 75 is described in the present exemplary embodiment, the structure is not limited to the above-described structure, and the third portion 113D can be continuous to the entrance portion 71 and substantially parallel to the entrance portion 71.

A method for wireless charging described in the present exemplary embodiment is not limited to a specific method, and an electromagnetic method, electric field method, or resonance method can be used.

While the structure in which the casing 7 has a substantially rectangular shape having longer and shorter sides, i.e., rectangle, is described in the present exemplary embodiment, the structure is not limited to the above-described structure, and the casing 7 can be square.

In the present exemplary embodiment, in a case in which the wireless power reception portion 8 is arranged at the connection portions 9A to 9G, only at least a portion of the wireless power reception portion 8 needs to be arranged at the connection portions 9A to 9G, and the remaining portion can be arranged at the entrance portion 71, the bottom portion 72, or the side portions 73.

A suitable method can be selected from various standards and methods for wireless transfer including near-field wireless transfer and long-distance wireless transfer, including the transfer speed, and applied as the wireless data transfer method described in the present exemplary embodiment. A transfer method using visible light or infrared light can be used.

While exemplary embodiments have been described, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Applications No. 2018-052276, filed Mar. 20, 2018, and No. 2018-052297, filed Mar. 20, 2018, which are hereby incorporated by reference herein in their entirety.

What is claimed is:

1. A radiographing apparatus, comprising:
a radiation detection panel configured to detect radiation;
a casing configured to enclose the radiation detection panel; and
a wireless power reception portion,
wherein the casing includes
an entrance portion through which the radiation enters,
a bottom portion arranged on an opposite side of the entrance portion,
a plurality of side portions, and
a connection portion configured to continuously connect the bottom portion and the side portions at a position located inside a first extension plane, which is an extension of a surface of the bottom portion, and a second extension plane, which is an extension of a surface of the side portions,
wherein the wireless power reception portion is arranged at the connection portion.

2. The radiographing apparatus according to claim 1, wherein the connection portion is approximately plate-shaped and approximately parallel to the bottom portion or approximately plate-shaped and inclined with respect to the bottom portion, and
wherein the wireless power reception portion is arranged inside the connection portion.

3. The radiographing apparatus according to claim 2, wherein the wireless power reception portion is arranged along an inner surface of the connection portion.

4. The radiographing apparatus according to claim 1, wherein the connection portion continuously connects two or more of the plurality of side portions and the bottom portion.

5. The radiographing apparatus according to claim 1, wherein the connection portion is inclined with respect to the bottom portion at an angle greater than 135 degrees and less than 180 degrees.

6. The radiographing apparatus according to claim 1, wherein the connection portion is curved outward in a protruded manner.

7. The radiographing apparatus according to claim 1, further comprising a circuit substrate enclosed in the casing,
wherein the wireless power reception portion is arranged not to overlap the circuit substrate when viewed from a radiation incident direction.

8. The radiographing apparatus according to claim 1, wherein the connection portion includes a window portion made of a non-conductive material at a position at which the wireless power reception portion is arranged.

9. The radiographing apparatus according to claim 1, wherein the connection portion includes a connection terminal that electrically connects to an entity external to the radiographing apparatus.

10. The radiographing apparatus according to claim 1,
wherein the casing includes a plurality of the connection portions, and
wherein the wireless power reception portion is not arranged on any of the plurality the connection portions.

11. A radiographing system, comprising:
a radiographing apparatus including
a radiation detection panel configured to detect radiation,
a casing configured to enclose the radiation detection panel, and
a wireless power reception portion,
wherein the casing includes
an entrance portion through which the radiation enters,
a bottom portion arranged on an opposite side of the entrance portion,
a plurality of side portions, and
a connection portion configured to continuously connect the bottom portion and the side portions at a position located inside a first extension plane, which is an extension of a surface of the bottom portion, and a second extension plane, which is an extension of a surface of the side portions,
wherein the wireless power reception portion is arranged at the connection portion, and
a wireless power transmission unit configured to transmit power to the radiographing apparatus,
wherein a size of the wireless power transmission unit does not extend beyond the first extension plane and the second extension plane when attached to the radiographing apparatus.

12. A radiographing apparatus, comprising:
a radiation detection panel configured to detect radiation; and
a casing configured to enclose the radiation detection panel,
wherein the casing includes a window portion,
wherein a wireless power reception portion and at least one of a wireless data transmission unit and a light source configured to indicate a state of the radiographing apparatus are arranged at the window portion, and
wherein at least one of the light source and the wireless data transmission unit is arranged to overlap both the window portion and the wireless power reception portion when viewed from a direction orthogonal to an outer surface of the window portion.

13. The radiographing apparatus according to claim 12, wherein the light source, the wireless data transmission unit, and the wireless power reception portion are arranged at the window portion.

14. The radiographing apparatus according to claim 12, wherein at least a portion of the window portion is made of a non-conductive material.

15. The radiographing apparatus according to claim 12, wherein at least a portion of the window portion is made of a light-transmissive material.

16. The radiographing apparatus according to claim 12, further comprising a light shielding layer between the radiation detection panel and the light source.

17. The radiographing apparatus according to claim 12, wherein the light source and the wireless power reception portion overlap each other.

18. The radiographing apparatus according to claim 12, wherein the light source and the wireless data transmission unit overlap each other.

19. The radiographing apparatus according to claim 12, further comprising a control unit configured to control the light source not to emit light when the wireless power reception portion receives power.

20. The radiographing apparatus according to claim 12, wherein a frequency band used in power reception by the wireless power reception portion and a frequency band used in data transfer by the wireless data transmission unit are different.

21. The radiographing apparatus according to claim 12, further comprising a control unit configured to prevent simultaneous operation by the wireless power reception portion and the wireless data transmission unit.

22. A radiographing apparatus, comprising:
a radiation detection panel configured to detect radiation; and
a casing configured to enclose the radiation detection panel,
wherein the casing includes a window portion,
wherein a wireless power reception portion and at least one of a wireless data transmission unit and a light source configured to indicate a state of the radiographing apparatus is arranged at the window portion,
wherein the wireless power reception portion and at least one of the light source and the wireless data transmission unit is arranged to overlap the window portion when viewed from a direction orthogonal to an outer surface of the window portion,
wherein the casing includes an entrance portion through which the radiation enters, a bottom portion arranged on an opposite side of the entrance portion, and a plurality of side portions, and
wherein the window portion is arranged on one or more of the bottom portion or the side portions.

23. A radiographing apparatus, comprising:
a radiation detection panel configured to detect radiation; and
a casing configured to enclose the radiation detection panel,
wherein the casing includes a window portion,
wherein a wireless power reception portion and one or more of a wireless data transmission unit and a light source configured to indicate a state of the radiographing apparatus are arranged at the window portion,
wherein the wireless power reception portion and at least one of the light source and the wireless data transmission unit is arranged to overlap the window portion when viewed from a direction orthogonal to an outer surface of the window portion, wherein the casing includes an entrance portion through which the radiation enters, a bottom portion arranged on an opposite side of the entrance portion, and a plurality of side portions, and wherein the window portion is located over two or more of the entrance portion, the side portions, or the bottom portion.

24. A radiographing system comprising:

a radiographing apparatus including a radiation detection panel configured to detect radiation, a casing configured to enclose the radiation detection panel, wherein the casing includes a window portion, wherein a wireless power reception portion and at least one of a wireless data transmission unit and a light source configured to indicate a state of the radiographing apparatus are arranged at the window portion; and wherein at least one of the light source and the wireless data transmission unit is arranged to overlap both the window portion and the wireless power reception portion when viewed from a direction orthogonal to an outer surface of the window portion; and a wireless power transmission unit configured to transmit power to the radiographing apparatus, wherein at least a portion of the wireless power transmission unit located near the window portion is made of a light-transmissive material.

* * * * *